(12) United States Patent
Stout et al.

(10) Patent No.: US 9,089,671 B2
(45) Date of Patent: Jul. 28, 2015

(54) SYSTEMS AND METHODS FOR SEALING A SEPTUM WITHIN A CATHETER DEVICE

(71) Applicants: Marty L. Stout, South Jordan, UT (US); S. Ray Isaacson, Roy, UT (US); Jonathan Karl Burkholz, Salt Lake City, UT (US)

(72) Inventors: Marty L. Stout, South Jordan, UT (US); S. Ray Isaacson, Roy, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 338 days.

(21) Appl. No.: 13/644,128

(22) Filed: Oct. 3, 2012

(65) Prior Publication Data

US 2013/0090608 A1    Apr. 11, 2013

Related U.S. Application Data

(60) Provisional application No. 61/544,162, filed on Oct. 6, 2011.

(51) Int. Cl.
*A61M 25/14* (2006.01)
*B23P 11/00* (2006.01)
(Continued)

(52) U.S. Cl.
CPC ....... *A61M 25/0097* (2013.01); *A61M 25/0606* (2013.01); *A61M 25/0693* (2013.01); *A61M 39/00* (2013.01); *A61M 5/14* (2013.01);
(Continued)

(58) Field of Classification Search
CPC ............. A61M 2039/0036; A61M 2039/0063; A61M 2039/0072; A61M 2039/009; A61M 2039/064; A61M 2039/0646; A61M 2039/066; A61M 2039/0666; A61M 2039/0673; A61M 2039/246; A61M 2039/266; A61M 2039/268; A61M 25/0693; A61M 25/003; A61M 25/0075; A61M 25/0029; A61M 25/0097; A61M 39/045; A61M 39/0693; A61M 39/0613; A61M 2206/10; A61M 2206/20; A61M 2005/14252; A61M 2005/14284
USPC .......................... 604/164.01, 167.04, 167.06
See application file for complete search history.

(56) References Cited

U.S. PATENT DOCUMENTS

| | | |
|---|---|---|
| 4,387,879 A | 6/1983 | Tauschinski |
| 4,449,693 A | 5/1984 | Gereg |

(Continued)

FOREIGN PATENT DOCUMENTS

| | | |
|---|---|---|
| CA | 2 133 053 A1 | 3/1995 |
| DE | 20 2009 009 602 U1 | 12/2009 |

(Continued)

OTHER PUBLICATIONS

Elson Silva, PhD, "Respecting Hydrology Science in the Patenting System," pp. 1-7, Jan. 13, 2011.

*Primary Examiner* — Nicholas Lucchesi
*Assistant Examiner* — Justin L Zamory
(74) *Attorney, Agent, or Firm* — Jeanne Lukasavage; Craig Metcalf; Kirton McConkie

(57) ABSTRACT

Systems and methods for sealing and venting a septum of an intravenous catheter device. Implementations of the present invention include a compact, molded septum that is retained within an inner lumen of a catheter adapter such that slowed or stopped flow of air and/or a fluid is permitted to pass between the compact septum and an inner wall surface of the catheter adapter via one or more fluid pathways. In some instances, a snap ring is provided to secure the position of the compact septum within the catheter adapter, a fluid pathway being provided through the snap ring.

16 Claims, 29 Drawing Sheets

(51) Int. Cl.
*A61M 25/00* (2006.01)
*A61M 25/06* (2006.01)
A61M 39/00 (2006.01)
A61M 5/14 (2006.01)

(52) U.S. Cl.
CPC .......... *A61M2039/0036* (2013.01); *A61M 2039/0063* (2013.01); *A61M 2039/0072* (2013.01); *A61M 2206/10* (2013.01); *A61M 2206/20* (2013.01); *Y10T 29/49959* (2015.01)

(56) References Cited

U.S. PATENT DOCUMENTS

| | | |
|---|---|---|
| 4,758,225 A | 7/1988 | Cox et al. |
| 4,773,552 A | 9/1988 | Boege et al. |
| 4,809,679 A | 3/1989 | Shimonaka et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2009/0287154 A1 | 11/2009 | Harding et al. |
| 2010/0036329 A1* | 2/2010 | Razack .................. 604/256 |
| 2010/0204648 A1 | 8/2010 | Stout et al. |
| 2010/0204675 A1 | 8/2010 | Woehr et al. |
| 2010/0222746 A1 | 9/2010 | Burkholz |

FOREIGN PATENT DOCUMENTS

| | | |
|---|---|---|
| EP | 1 679 043 A1 | 7/2006 |
| WO | 99/34849 | 7/1999 |
| WO | 2007/044878 A2 | 4/2007 |
| WO | 2008/052790 A2 | 5/2008 |
| WO | 2009/114833 A1 | 9/2009 |
| WO | 2010/093791 A1 | 8/2010 |
| WO | 2012/002015 A1 | 1/2012 |

* cited by examiner

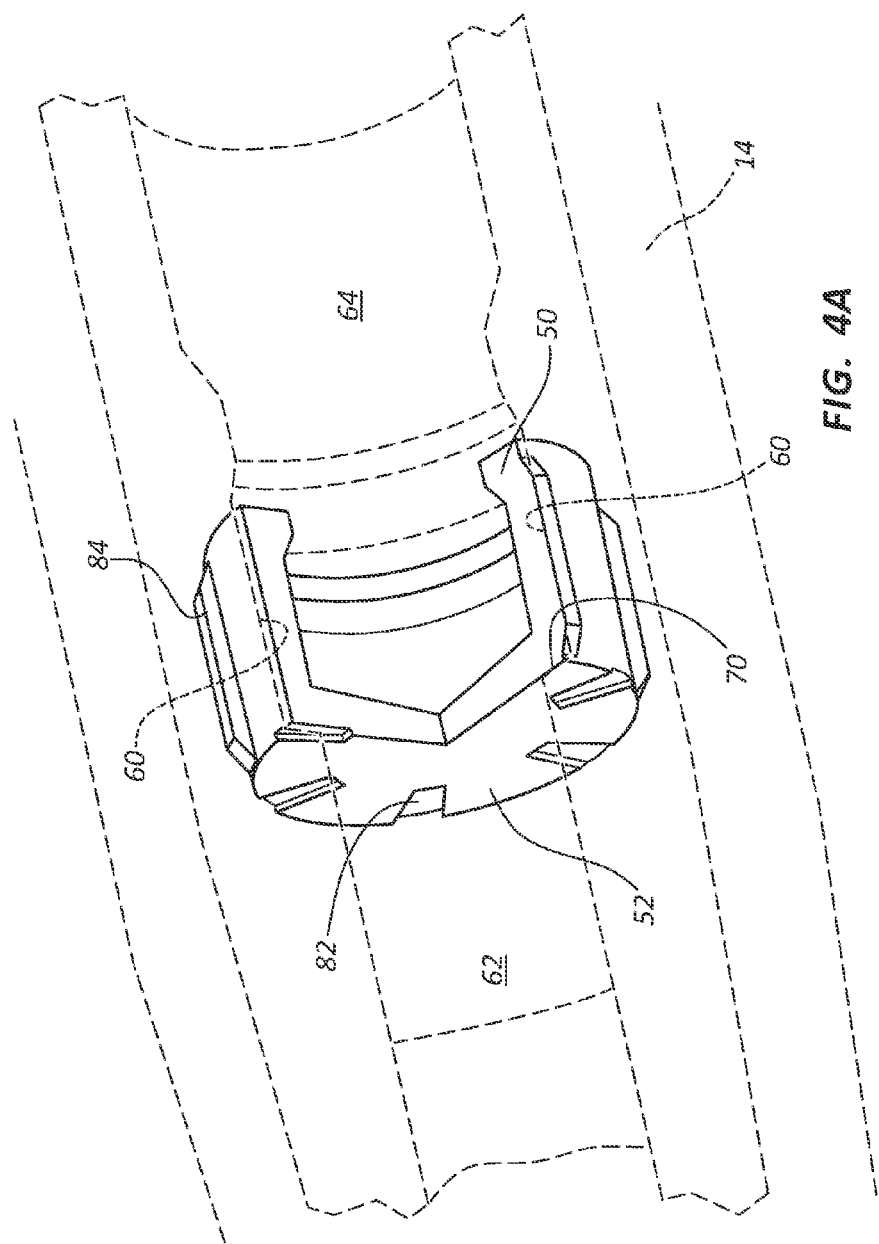

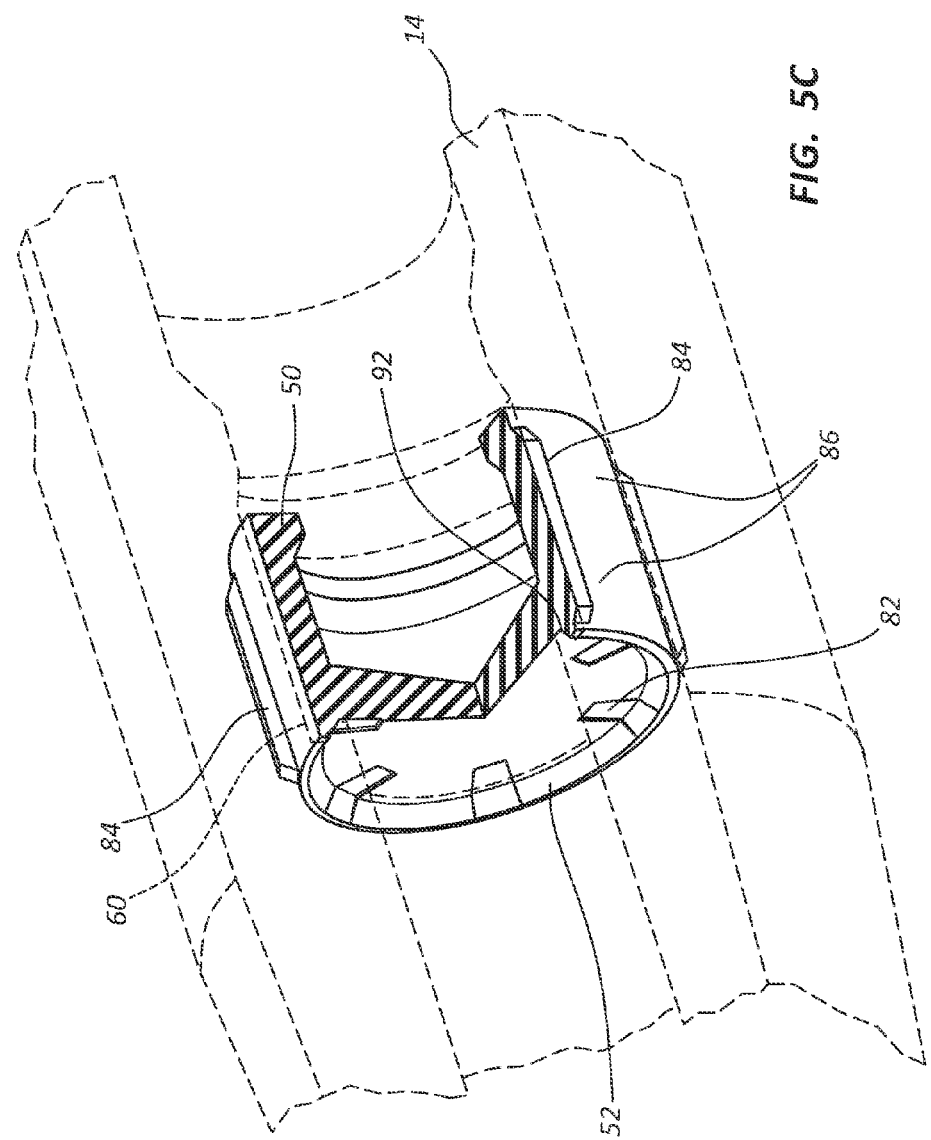

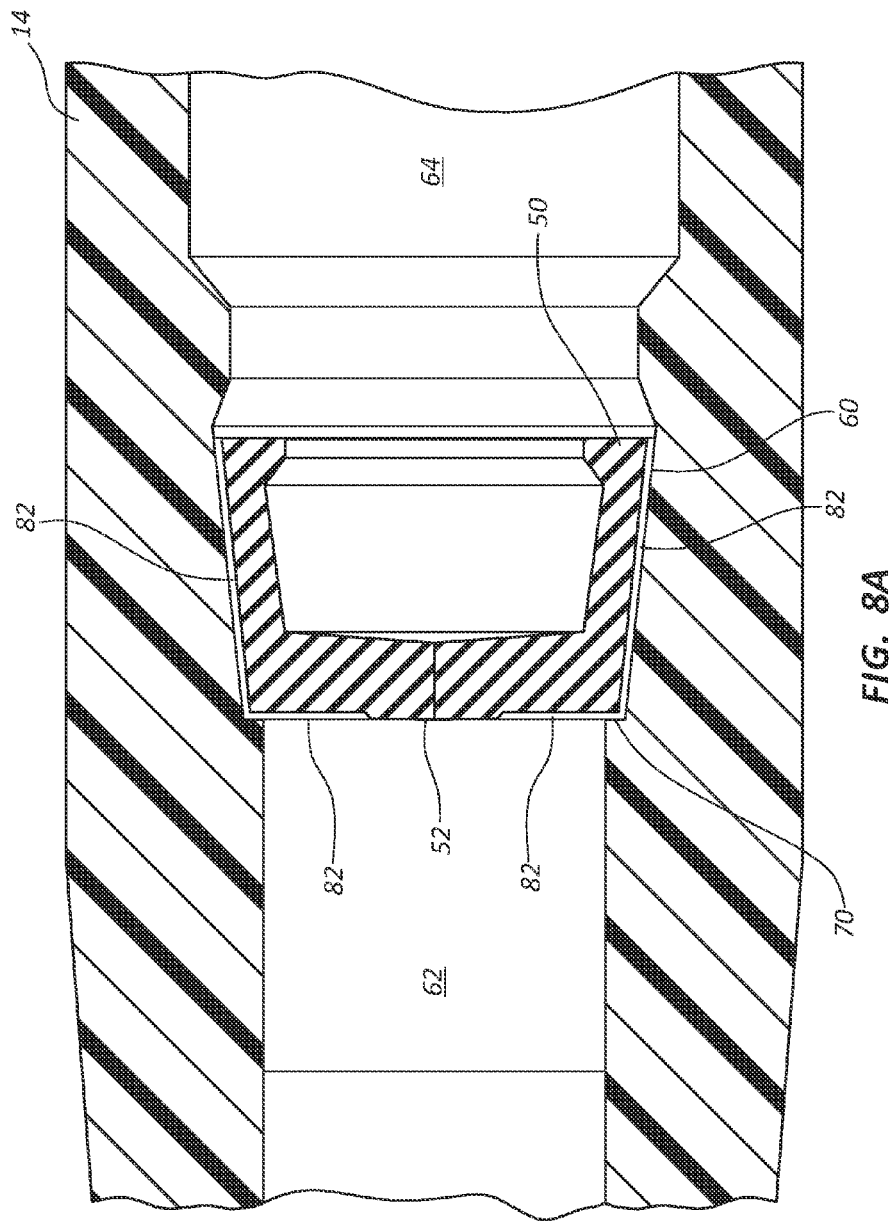

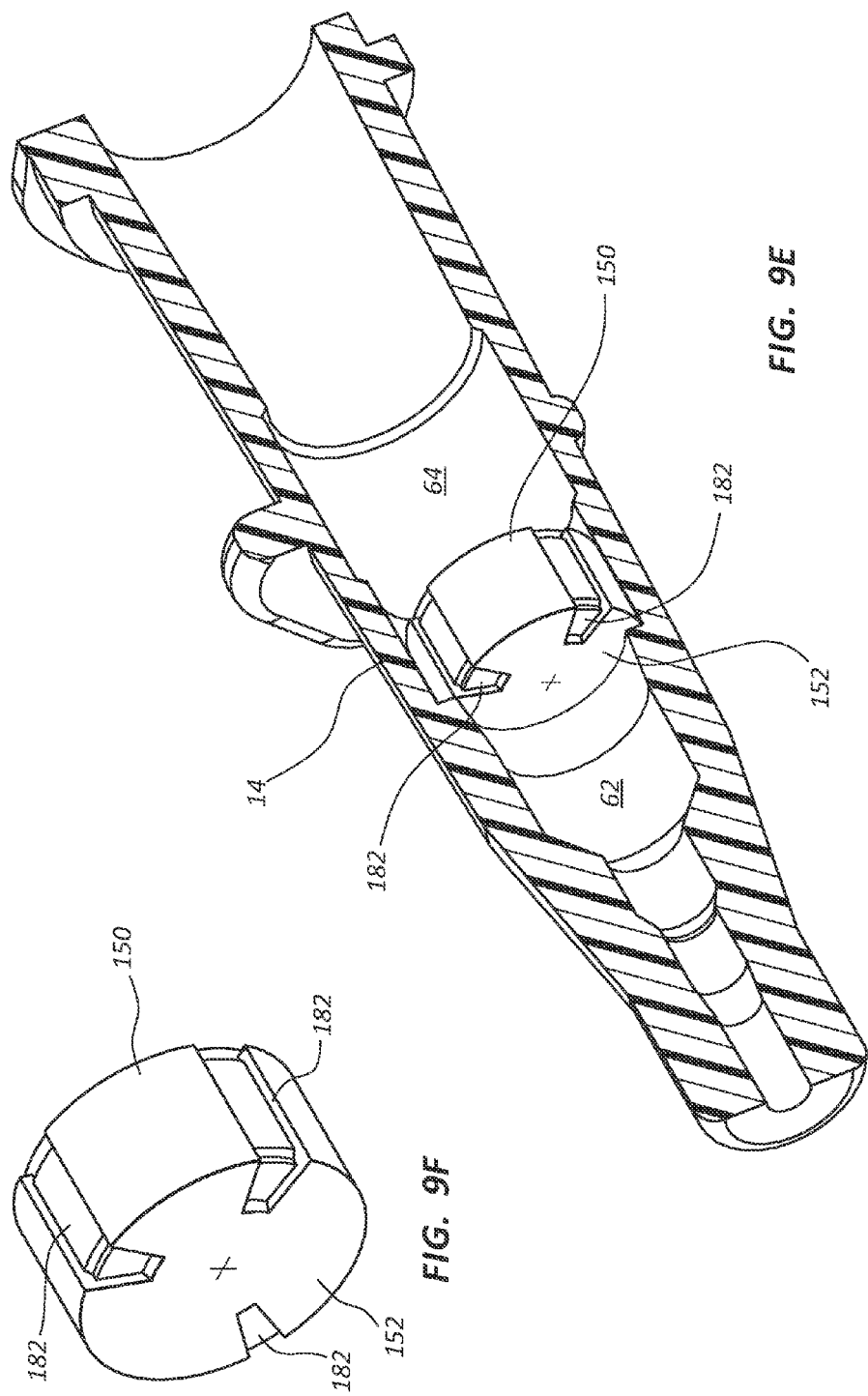

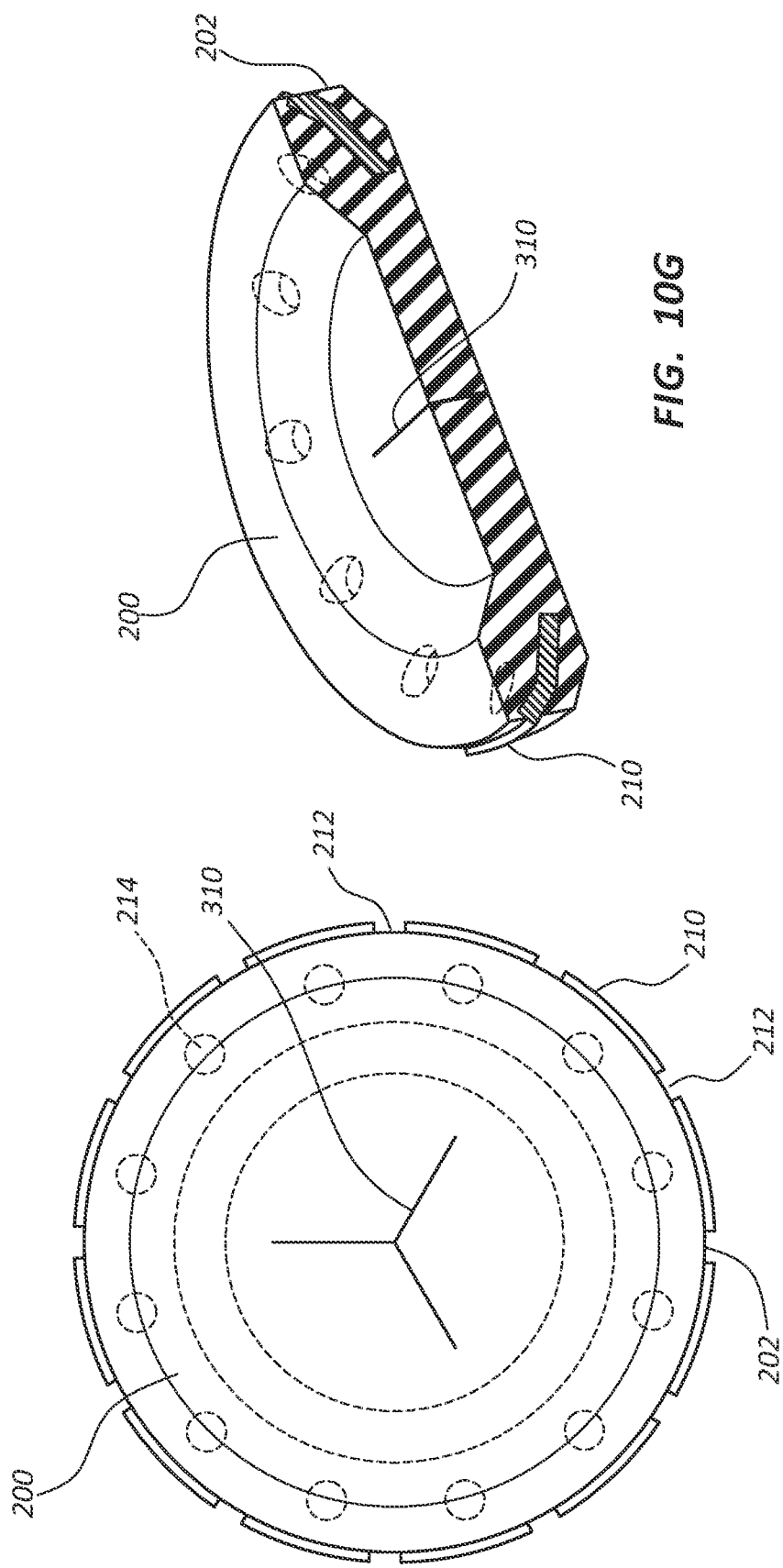

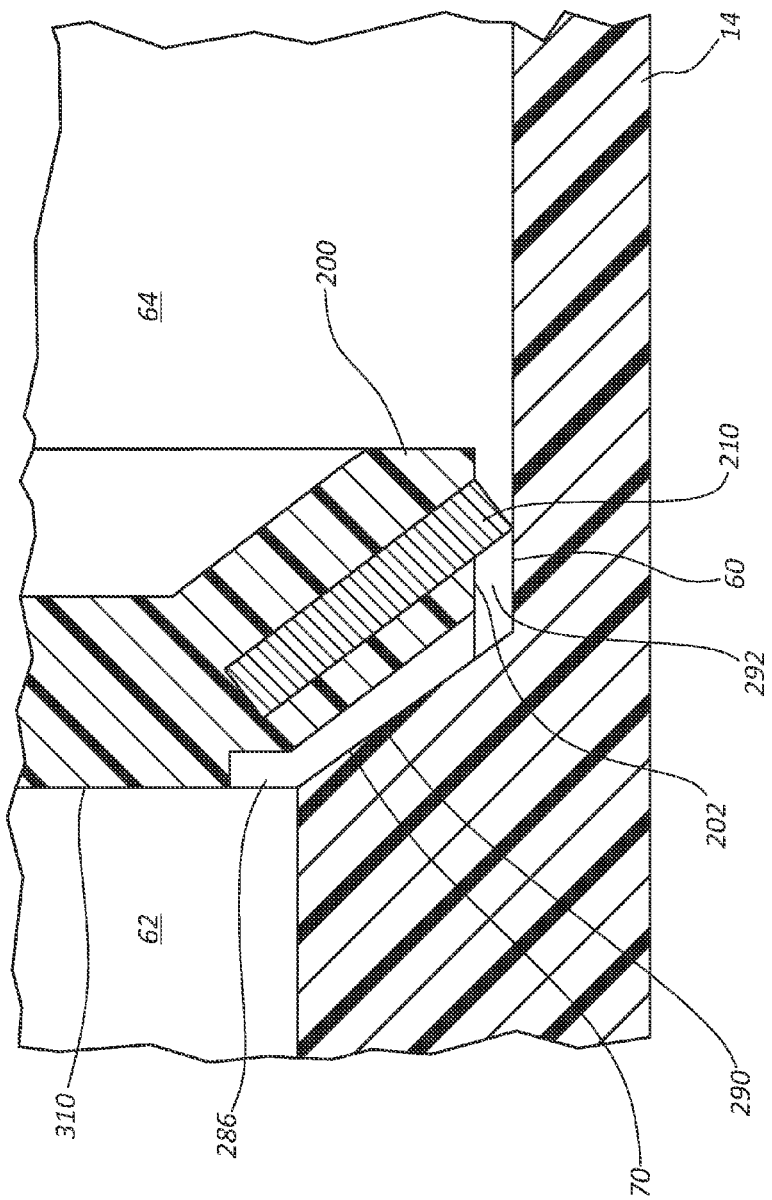

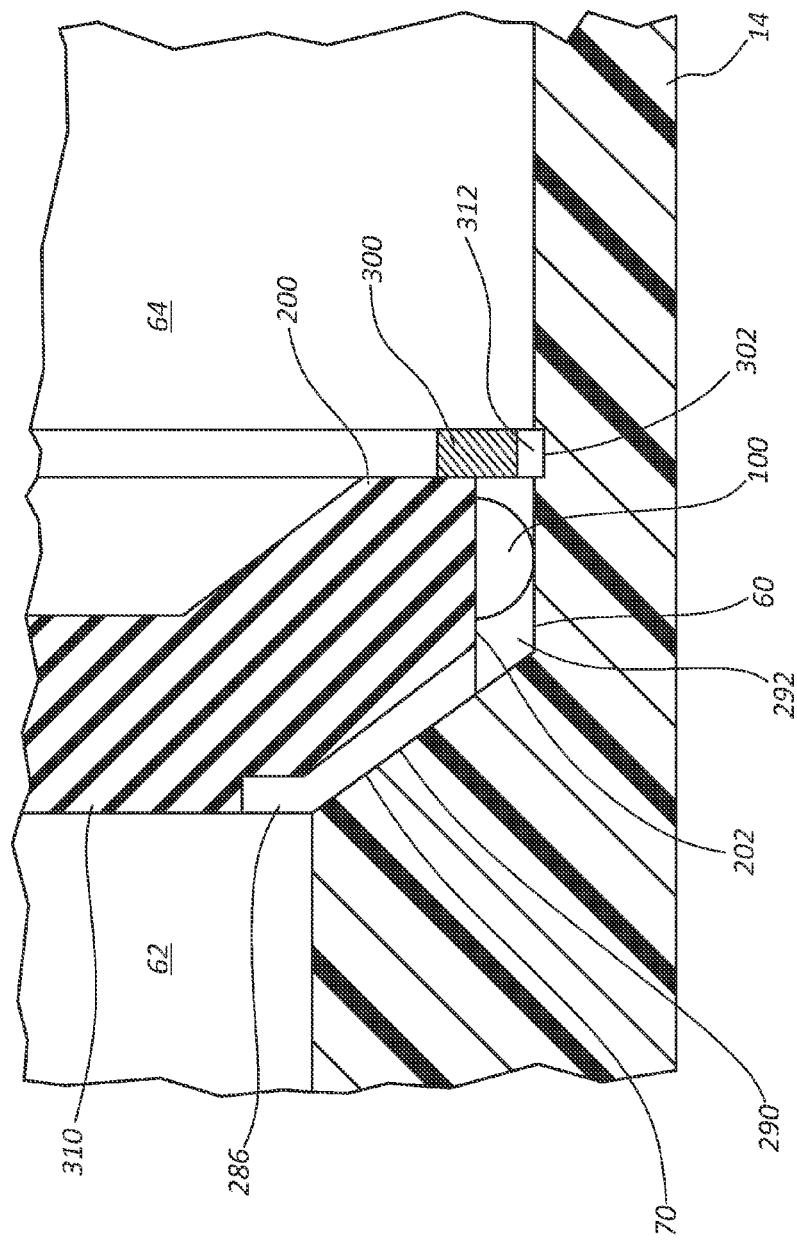

SYSTEMS AND METHODS FOR SEALING A SEPTUM WITHIN A CATHETER DEVICE

RELATED APPLICATIONS

This application claims priority to U.S. Provisional Patent Application Ser. No. 61/544,162, filed Oct. 6, 2011, and entitled SYSTEMS AND METHODS FOR SEALING A SEPTUM WITHIN A CATHETER DEVICE, which is incorporated herein in its entirety.

BACKGROUND OF THE INVENTION

Catheters are commonly used for a variety of infusion therapies. For example, catheters are used for infusing fluids, such as normal saline solution, various medicaments, and total parenteral nutrition into a patient; withdrawing blood from a patient; or monitoring various parameters of the patient's vascular system. Catheters are typically coupled to a catheter adapter that supports catheter and provides for an attachment to IV tubing. Generally, following placement of the catheter into the vasculature of a patient, the catheter adapter may be coupled to a fluid source via a section of IV tubing to infuse fluids into the patient.

In order to verify proper placement of the catheter in the blood vessel, the clinician generally confirms that there is "flashback" of blood from the patient's vasculature into a flashback chamber of the catheter or catheter adapter. Once proper placement of the catheter is confirmed, the clinician must attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing.

A common, yet undesirable practice is to permit blood to temporarily and freely flow from the catheter adapter while the clinician locates and couples the IV tubing to the catheter adapter. Another common practice is to attach the catheter adapter to the IV tubing prior to placing the catheter into the vein of the patient. While this method may prevent undesirable exposure to blood, positive pressure from the IV tubing into the catheter does not permit desirable flashback and thus reduces a clinician's ability to confirm proper catheter placement.

Some catheter systems utilize a valve or septum disposed within the catheter adapter, as a barrier to control fluid flow through the catheter. Generally, a seal is provided between the septum and an inner surface of the catheter adapter thereby preventing flow of fluids around the septum. In some systems, a slit or perforation is provided in the septum whereby a controlled amount of fluid is permitted to bypass the septum. In other systems, a system of channels is provided between the outer surface of the septum and the inner surface of the catheter adapter, thereby providing a fluid pathway around the exterior of the septum. However, the methods whereby the septum of these systems is sealed within the catheter adapter are prone to undesirable leakage based upon the various compressive forces which are exerted upon a septum during catheterization and subsequent infusion procedures.

Accordingly, there is a need in the art for a catheter assembly that permits controlled, desirable flashback without undesirable leakage. Such a catheter assembly is disclosed herein.

BRIEF SUMMARY OF THE INVENTION

In order to overcome the limitations discussed above, the present invention relates to systems and methods for sealing and venting a septum within a catheter device. In particular, the present invention relates to systems and methods for sealing and venting a septum within a catheter device and providing a desired rate of fluid flow around the septum.

In some implementations of the present invention, a catheter device is provided which incorporates a septum having sealing and venting features. In particular, in some embodiments a septum is provided having a chamfered sealing surface which forms a seal with a chamfered distal edge of a catheter adapter. Some aspects of the invention further include a fluid channel comprising a portion of the septum membrane and sealing surface, wherein a fluid is permitted to flow through the fluid channel to bypass the septum in a controlled manner.

In other implementations, a septum is provided having a sealing surface on an inner diameter of the septum membrane, wherein the distal edge of the catheter adapter comprises a hook or lip configuration. In some aspects, a non-sealing centering rib is provided on the sealing surface. In other aspects, a fluid channel is provided on the septum membrane and sealing surface, thereby permitting fluid flow between the septum in the catheter adapter. Further still, in some implementations the non-sealing venting and centering ribs comprise domes, bumps or other shaped features.

In some implementations, a septum is provided having a tapered sealing area that does not comprise the outermost circumferential surface of the septum. Rather, the outermost circumferential surface of the septum is spaced from the inner surface of the catheter adapter thereby permitting fluid flow between the outermost circumferential surface of the septum and the inner surface of the catheter adapter. Further, a fluid channel is provided between the tapered sealing area and a distal edge of the catheter adapter to permit fluid passage between the proximal and distal chambers of the catheter adapter.

In other implementations, a septum is provided having a chamfered outer circumferential surface. The chamfered outer circumferential surface further comprises a plurality of fluid channels to permit passage of fluid between the septum and the inner surface of the catheter adapter.

Some aspects of the present invention further include a septum having a single large vent or fluid channel to facilitate passage of fluid between the septum and the inner surface of the catheter adapter. Other aspects of the invention include a septum having a plurality of large vents thereby enabling a user to calibrate the septum and/or catheter device for a desired rate of fluid flow.

Further still, some implementations of the present invention include an insert molded valve or septum system. The molded septum includes an outer circumferential surface which includes a plurality of centering features, such as bumps. The molded septum is generally dish shaped wherein the septum has a thin profile thereby allowing for the use of a shortened actuator. The thin profile of the molded septum further allows for good flush-ability and may permit a shorter catheter adapter, cannula, barrel and packaging. In some implementations, the molded septum is retained within the catheter adapter via a retention ring, such as a snap ring.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

Embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

DETAILED DESCRIPTION OF THE INVENTION

Figure 1:
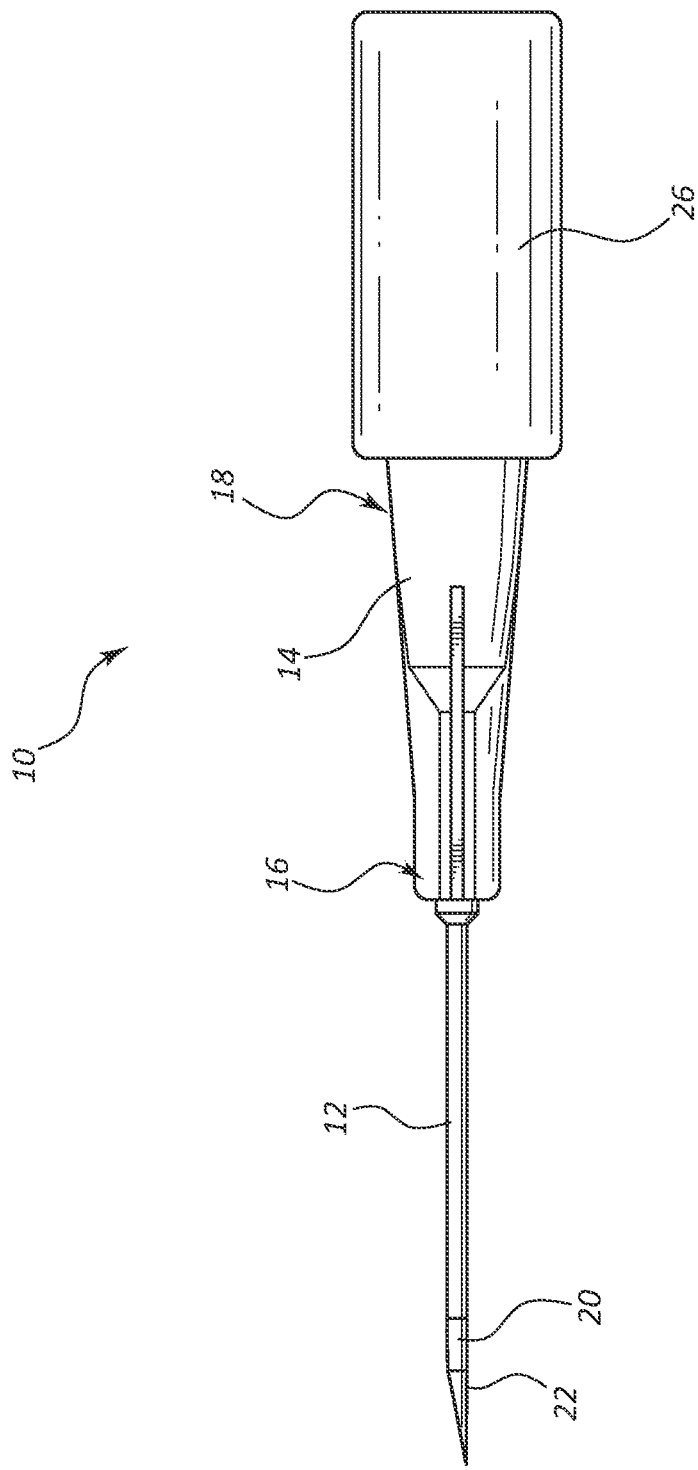
FIG. 1 is a perspective view of an intravascular device in accordance with a representative embodiment of the present invention.

Referring now to FIG. 1, an intravascular device 10 is illustrated. The intravascular device 10 generally includes a catheter 12 coupled to a distal end 16 of a catheter adapter 14. The catheter 12 and the catheter adapter 14 are integrally coupled such that an inner lumen of the catheter adapter 14 is in fluid communication with an inner lumen of the catheter 12. The catheter 12 generally comprises a biocompatible material having sufficient rigidity to withstand pressures associated with insertion of the catheter into a patient.

In some embodiments, as shown, the catheter 12 is an over-the-needle catheter that is made of a flexible or semi-flexible polymer material and which may be used in combination with a rigid introducer needle 22. The rigid introducer needle 22 enables the insertion of the non-rigid over-the-needle catheter into a patient. The introducer needle 22 can be coupled to a needle hub 26 that is selectively coupled to the proximal end 18 of the catheter adapter 14. The introducer needle 22 is typically inserted through the catheter 12 such that a tip of the needle 22 extends beyond the tapered tip 20 of the catheter 12. Insertion of the introducer needle 22 into the vein of the patient creates an opening in the vein through which the tapered tip 20 of the catheter 12 is inserted. The outer surface of the tapered tip 20 enables gradual insertion of the catheter 12 into the opening.

In other embodiments, the catheter 12 is not an over-the-needle catheter, but comprises a rigid, polymer material, such as vinyl. Rigid catheters can include a beveled cutting surface that is utilized to provide an opening in a patient to permit insertion of the catheter 12 into the vascular system of the patient. Accordingly, in some embodiments, the catheter 12 comprises a metallic material, such as titanium, stainless steel, nickel, molybdenum, surgical steel, and alloys thereof. Still, in other embodiments, surgically implanted catheters may also be used in combination with the present invention.

In some embodiments, catheter 12 is a peripheral-type intravenous catheter that generally comprises a short or truncated catheter for insertion into a small peripheral vein. Such catheters generally comprise a diameter of about a 14-gauge catheter or smaller (on a Stubs scale), and are between about 13 mm to 52 mm in length. Peripheral intravenous catheters are typically designed for temporary placement. The short length of the catheter facilitates convenient placement of the catheter. In other embodiments, catheter 12 is a midline or central catheter, which may be longer and used for more extended periods.

Figure 2:
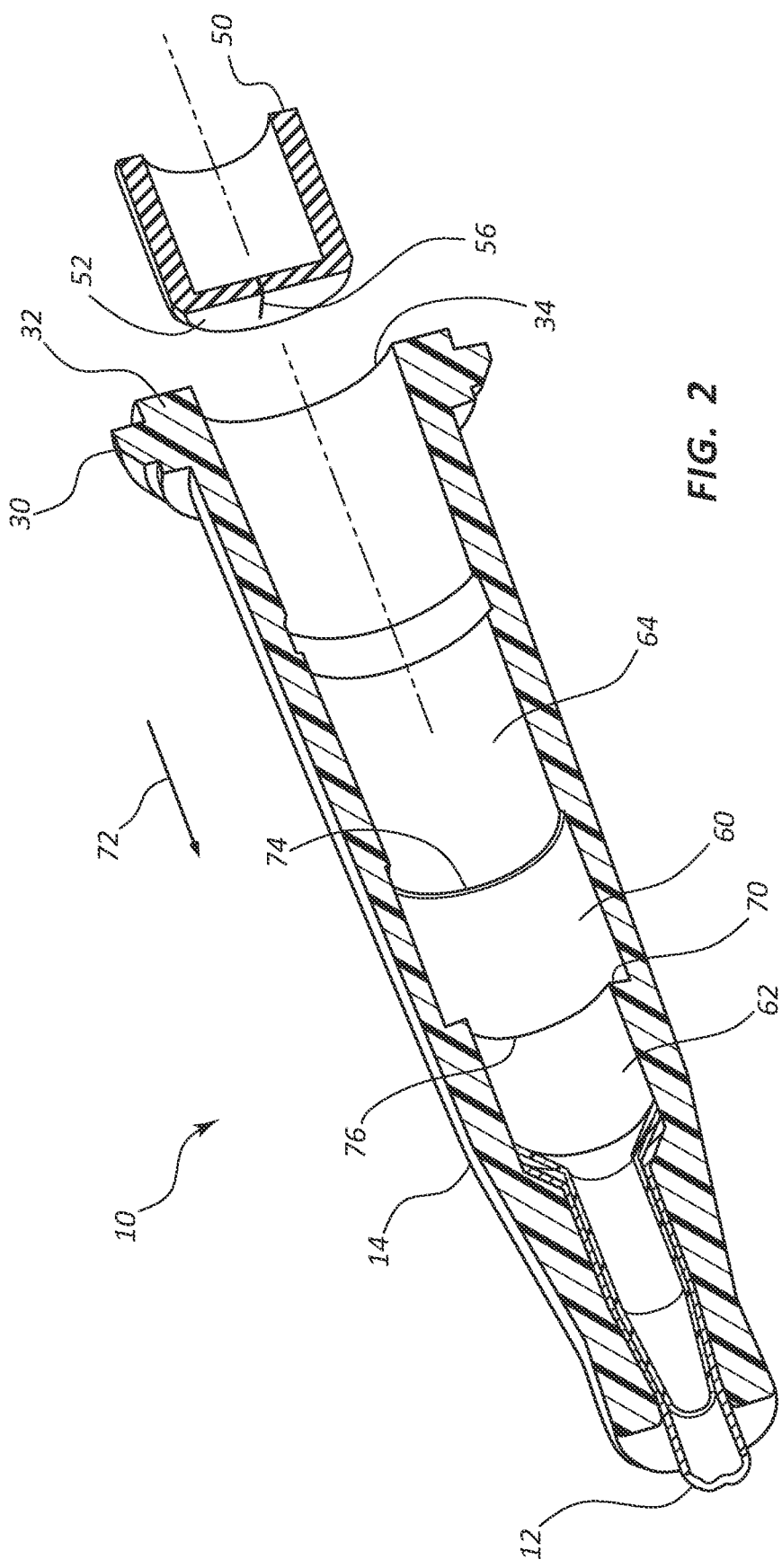
FIG. 2 is an exploded cross-sectioned view of an intravascular device in accordance with a representative embodiment of the present invention.

Referring now to FIG. 2, an exploded, cross-sectional view of an intravascular device 10 is shown. In some embodiments, intravascular device 10 comprises a catheter adapter 14 having an inner surface 60 for receiving a septum 50. In some embodiments, inner surface 60 comprises a recessed groove having a length and depth sufficient to accommodate the length and outer diameter of septum 50. A distal ledge 70 of inner surface 60 is generally configured to abut membrane 52 of septum 50, thereby preventing membrane 50 from shifting within catheter adapter 14 in a proximal direction 72. Distal ledge 70 may also provide a sealing surface for septum 50, whereby the distal chamber 62 is sealedly isolated from proximal chamber 64. Generally, septum 50 comprises a hyperelastic material that, when assembled, interfaces with inner surface 60 through interference fit. However, some embodiments of the present invention provide a compact septum design that is retained in catheter adapter 14 via a snap ring, as discussed below.

Embodiments of the present invention generally provide a catheter adapter having a septum that is retained within the inner lumen of the catheter adapter in such a manner as to provide slowed or stopped flow of a fluid and/or air through the inner lumen. In some instances, a fluid pathway is provided between the septum and an inner wall of the catheter adapter, wherein the fluid pathway is configured to permit passage of air and/or fluid at a desired rate. In some instances, a cross-sectional area of the fluid pathway is selected to permit passage of air at a desired rate, while preventing passage of a fluid. In other instances, a cross-sectional area of the fluid pathway is selected to permit passage of air at a desired rate, while permitting passage or fluid at a slowed or reduce rate. In this manner, flashback and containment of fluids may be controlled based upon the geometries and dimensional parameters of the fluid pathway.

In some instances, a fluid pathway comprises a vent or channel provided in the inner surface of the catheter adapter at a position adjacent to the septum. In other embodiments, a fluid pathway comprises a vent or channel provided on the outer surface of the septum. Further, in some instances a fluid pathway comprises a vent or channel provided through a portion of a snap ring, wherein the snap ring secures the position of the septum within the inner lumen of the catheter adapter. Some embodiments of the present invention further comprise a centering feature on a circumferential surface of the septum, wherein the centering feature comprises a vent or channel to permit passage of a fluid or air. Further still, in some embodiments a fluid pathway comprises a plurality of vents and/or channels provide as part of the septum, the catheter adapter and/or the snap ring.

Figure 3A:
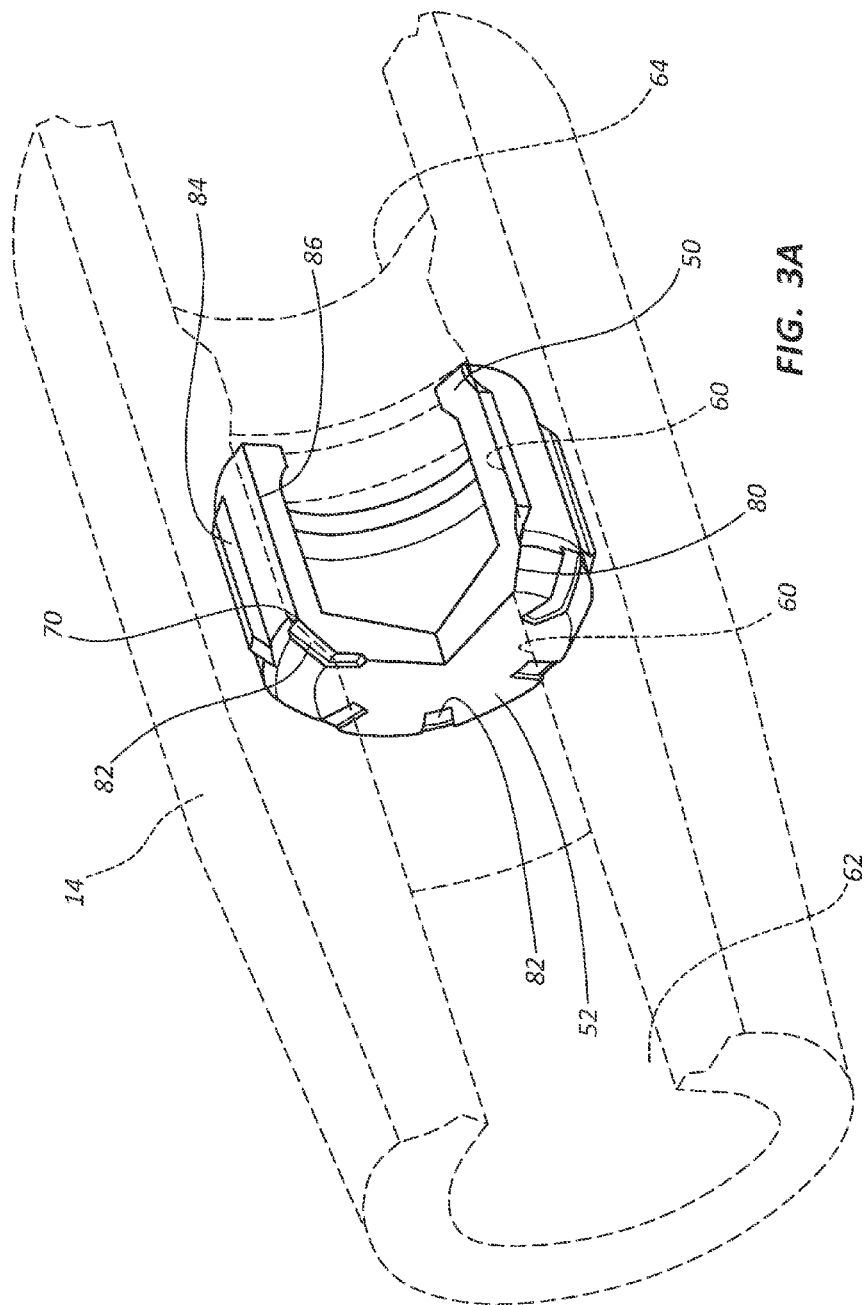
FIG. 3, shown in parts A-B, shows a septum having a tapered sealing surface in accordance with a representative embodiment of the present invention.

For example, referring now to FIG. 3A, in some embodiments membrane 52 of septum 50 comprises a tapered sealing surface 80. Tapered sealing surface 80 and membrane 52 further comprise fluid channels 82 through which fluid flows from distal chamber 62 to proximal chamber 54 following catheterization. In some embodiments, distal ledge 70 is further chamfered thereby providing a surface against which tapered sealing surface 80 is abutted to form a seal between septum 50 and distal ledge 70 of catheter adapter 14.

Figure 3B:
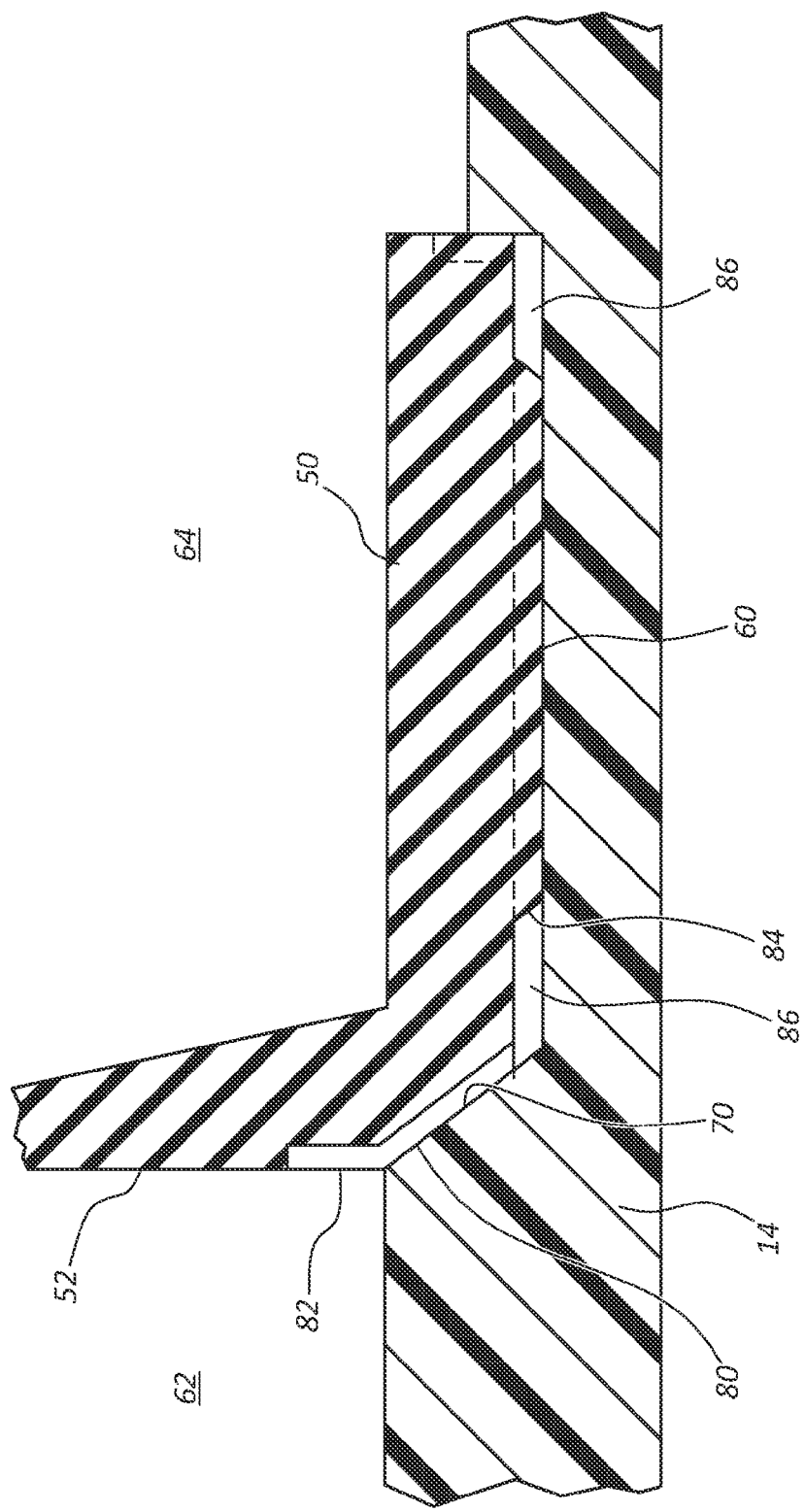

In some embodiments, septum 50 further comprises non-sealing, centering stand-off ribs 84. Ribs 84 provide a spacing function whereby a gap 86 is provided between the outer surface of septum 50 and inner surface 60, as shown in FIGS. 3A and 3B. Ribs 84 further provide a centering function whereby septum 50 is centered within inner surface 60. In some embodiments, ribs 84 further provide a retaining function, wherein ribs 84 engage a groove (not shown) located on inner surface 60. Ribs 84 are axially spaced around the outer circumference of septum 50 thereby providing significant gaps 86 for fluid flow around the outer circumference of septum 50. In some embodiments, the number and/or width of ribs 84 are adjusted to increase or decrease the possible flow rate around the outer circumference of septum 50. In other embodiments, the width and depth of channels 82 are adjusted to increase or decrease the possible flow rate between distal chamber 62 and proximal chamber 64. Accordingly, the flow dynamics of septum 50 may be adjusted as desired.

Figure 4B:
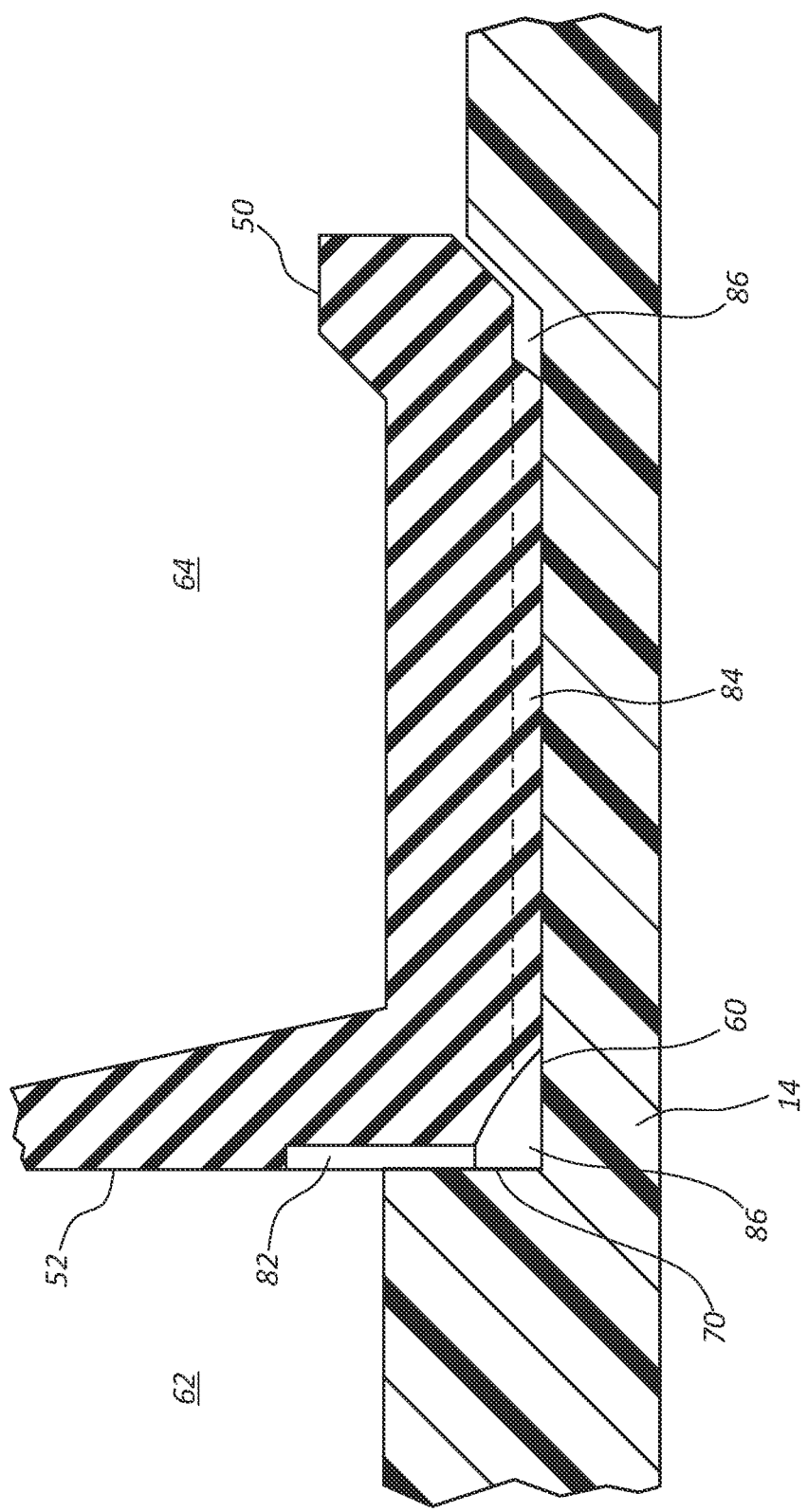
FIG. 4, shown in parts A-C, shows a septum having a vertical front face sealing surface in accordance with a representative embodiment of the present invention.

Referring now to FIGS. 4A and 4B, in some embodiments septum 50 comprises a planar membrane 52, and catheter adapter 14 comprises a vertical front face distal ledge 70. Accordingly, a vertical seal is formed between membrane 52 and distal ledge 70. In some embodiments, septum 50 further comprises channels 82 and ribs 84 to center septum 50 within inner surface 60 and provide fluid flow between distal chamber 62 and proximal chamber 64.

Figure 4C:
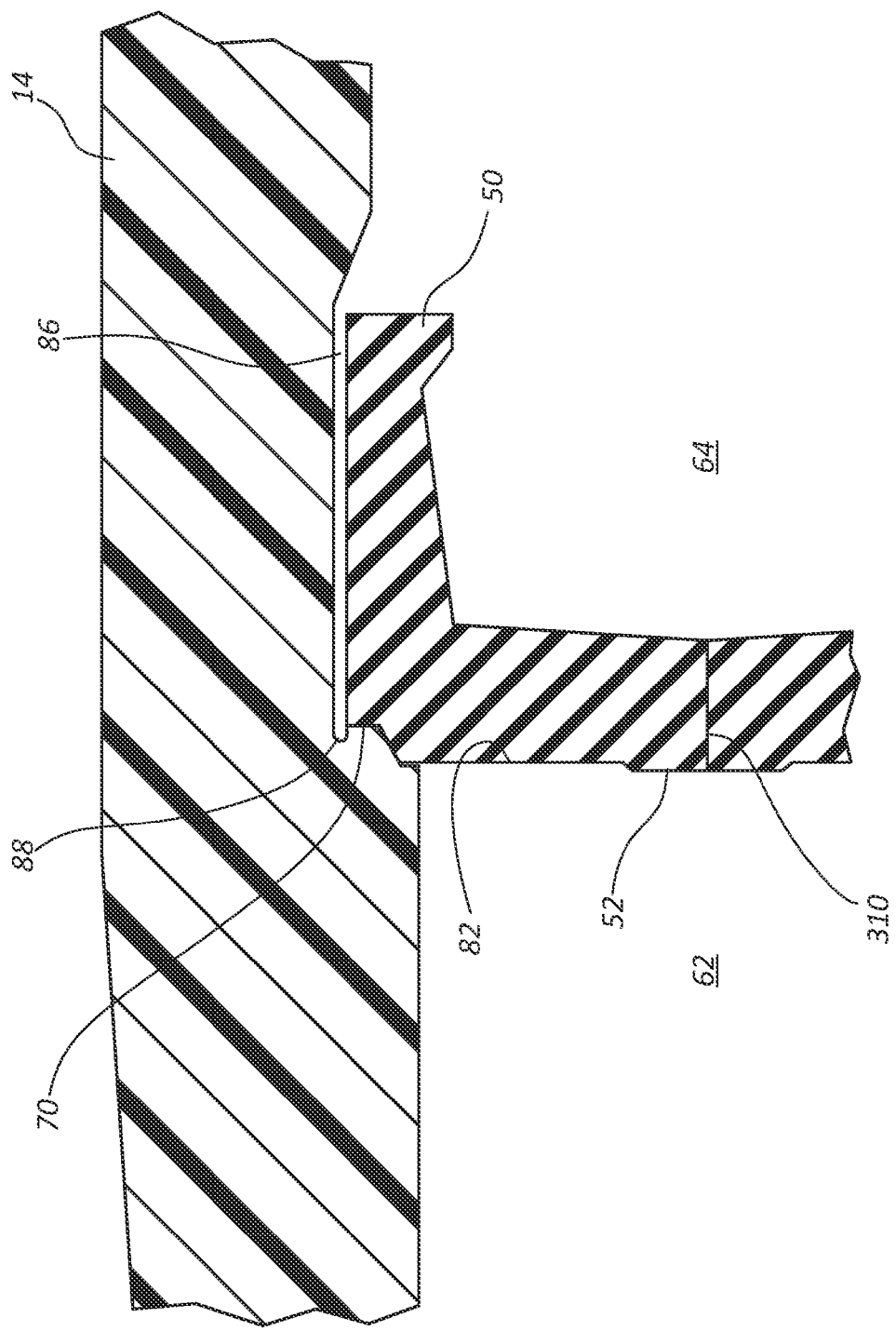

With reference to FIG. 4C, in some embodiments a small gap 88 is provided between a portion of distal ledge 70 and fluid channel or gap 86. Small gap 88 is provided to prevent stagnation of fluid between catheter adapter 14 and septum 50. In particular, small gap 88 diverts the fluid path of blood or other fluids flowing through channel 82 and gap 86. Thus, small gap 88 prevents over concentration of fluids and/or coagulation of blood within fluid channel 86.

Figure 5A:
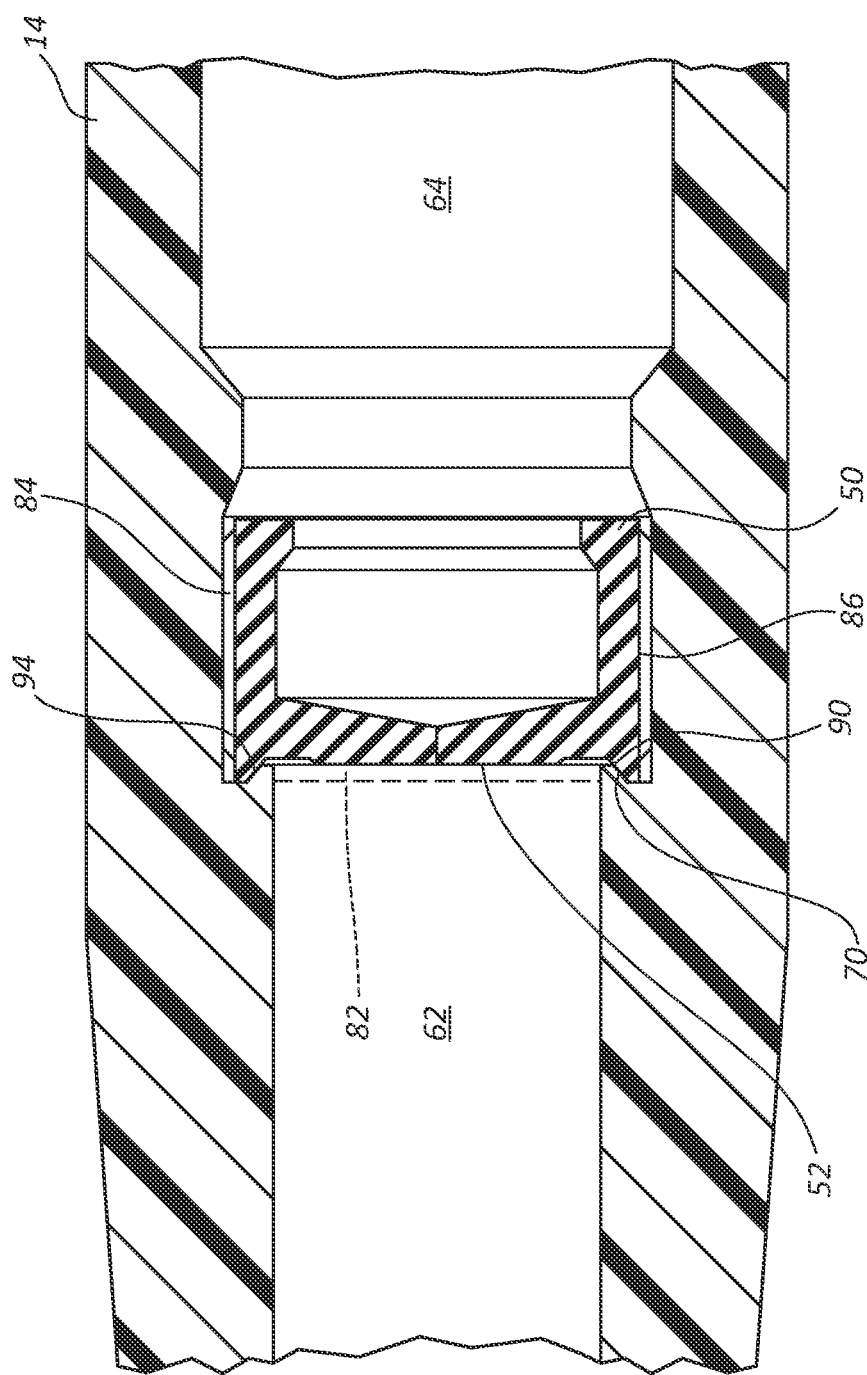
FIG. 5, shown in parts A-C, shows a septum having an inner diameter sealing surface in accordance with a representative embodiment of the present invention.
Figure 5B:
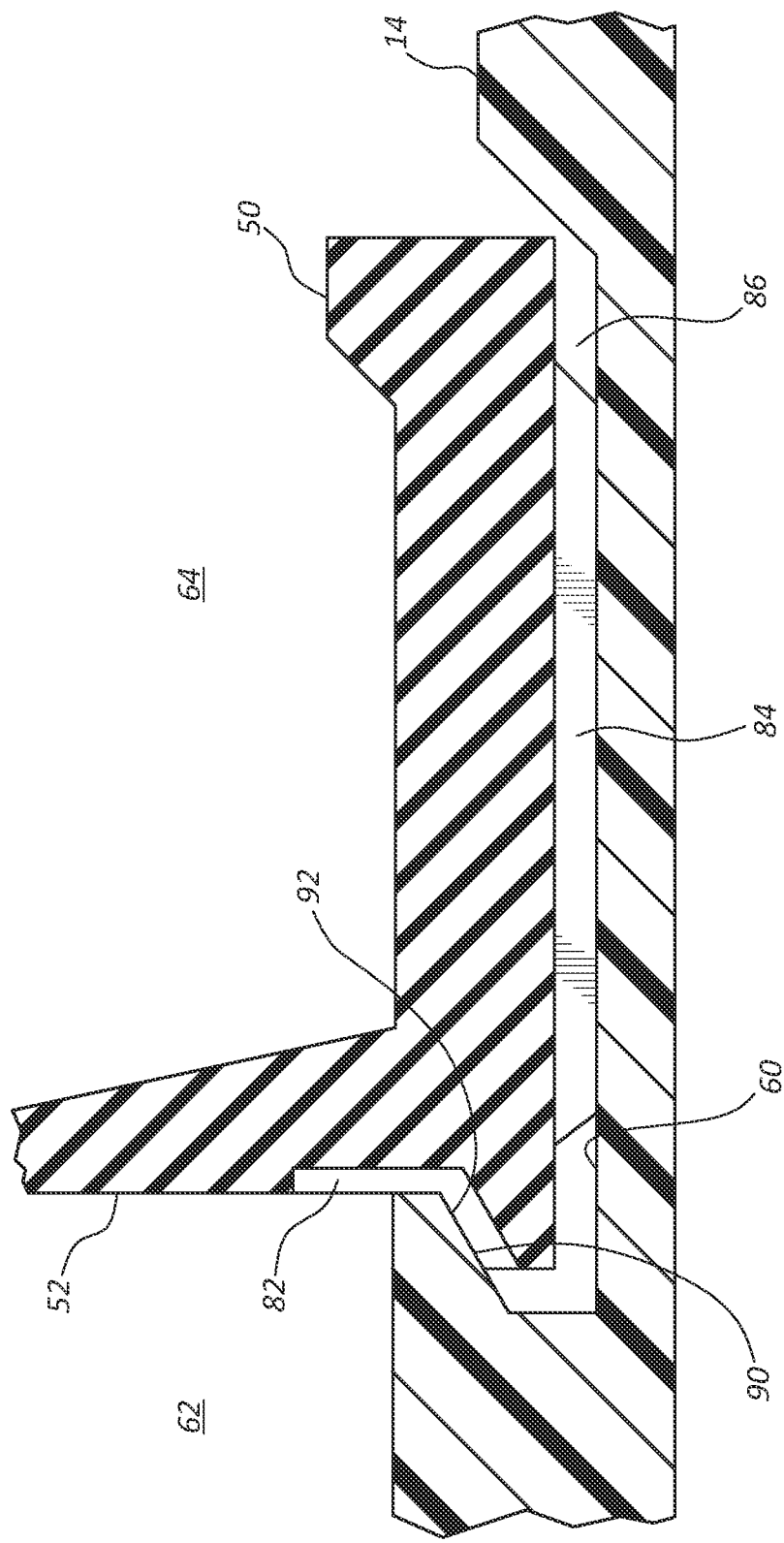

Referring now to FIGS. 5A-5C, in some embodiments distal ledge 70 comprises a hook or lip, as shown. Accordingly, membrane 52 of septum 50 is modified to comprise a compatible sealing surface 90. For example, in some embodiments sealing surface 90 comprises an internal taper or chamfer on an inner diameter surface of the septum, configured to interface with the hook or lip surface of distal ledge 70. In some embodiments, sealing surface 90 further comprises vent ribs 92 which provide spacing and thereby permit fluid flow between distal ledge 70 and portions of sealing surface 90. In other embodiments, distal ledge 70 further comprises vent ribs 94 which provide spacing and thereby permit fluid flow between distal ledge 70 in sealing surface 90 of septum 50. Further still, in some embodiments septum 50 comprises ribs 84 to provide additional spacing between inner surface 60 and the outer circumference of septum 50, as shown in FIGS. 5A and 5B.

Figure 6A:
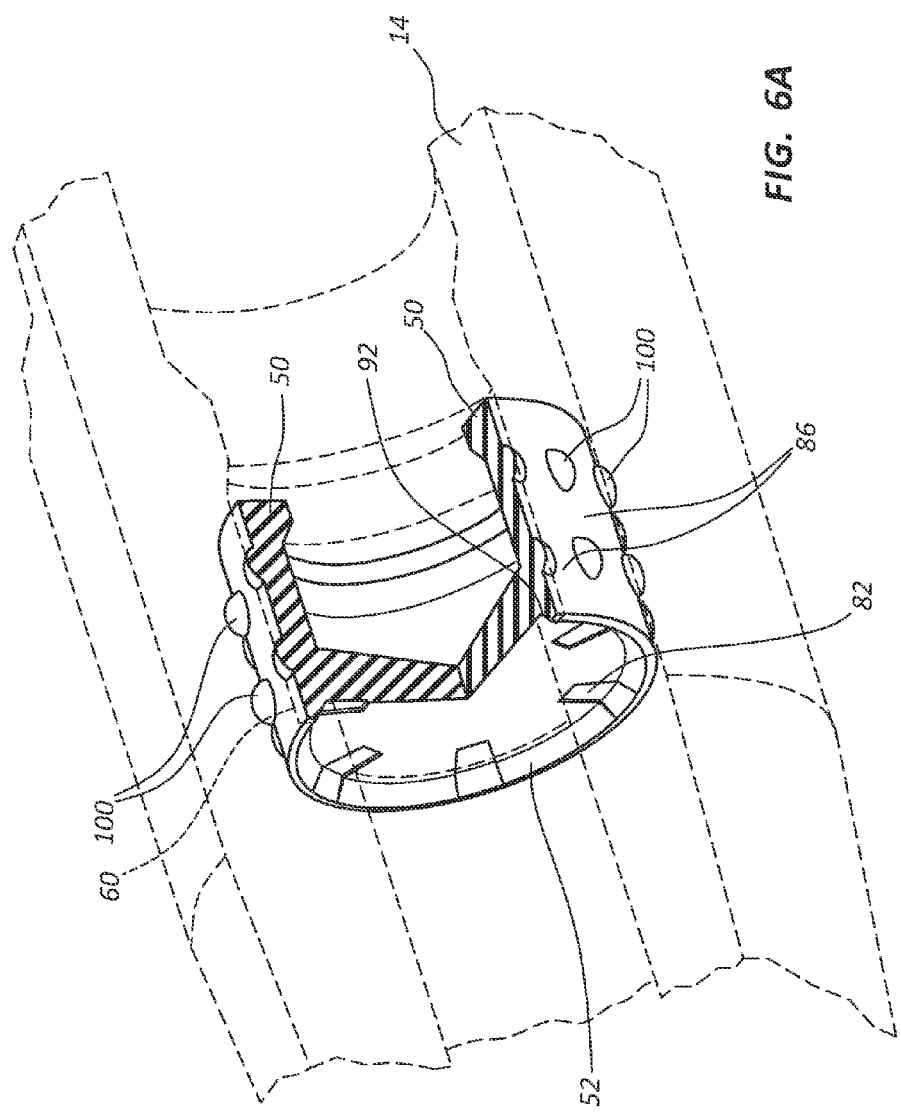
FIG. 6, shown in parts A-B, shows a septum having dome centering features in accordance with a representative embodiment of the present invention.
Figure 6B:
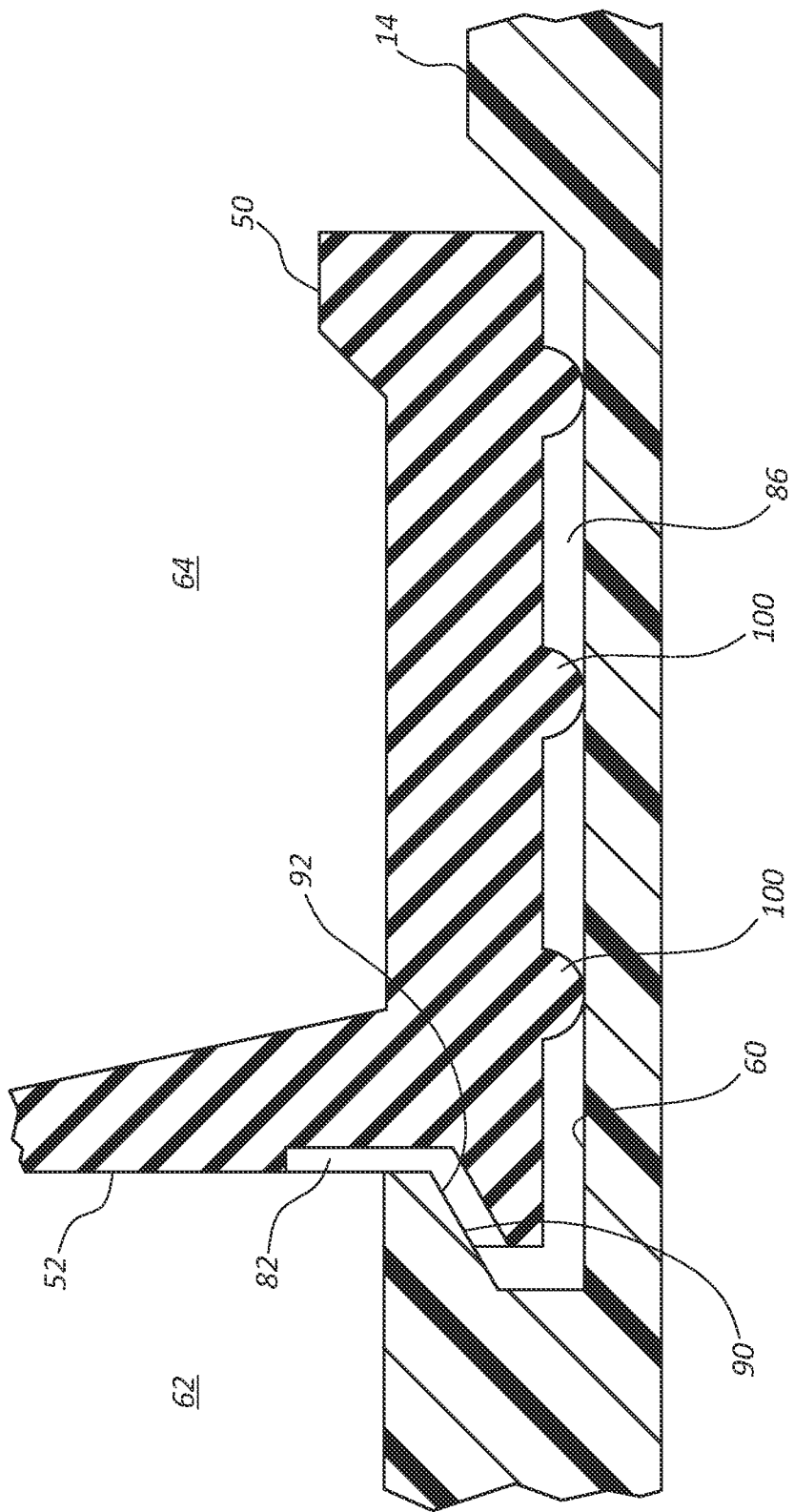

With reference to FIGS. 6A-6B, in some embodiments ribs 84 are replaced with domes, bumps or other shaped centering features 100 to provide spacing between the outer surface of septum 50 and inner surface 60. Accordingly, shape features 100 provide a gap 86 to permit fluid flow between septum 50 and inner surface 60.

Figure 7A:
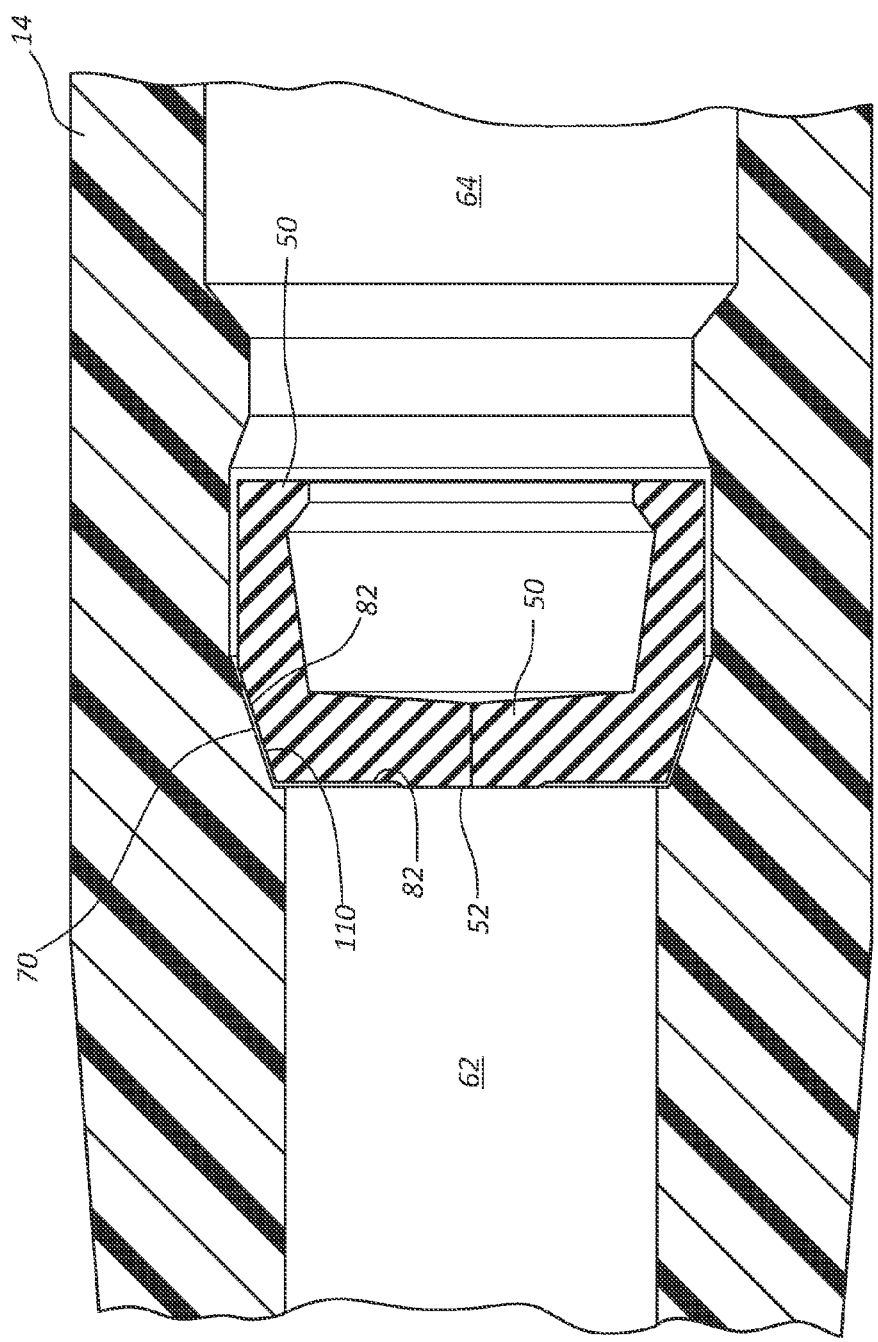
FIG. 7, shown in parts A-B, shows a septum having a tapered sealing surface that is not on the outermost circumference of the septum in accordance with a representative embodiment of the present invention.
Figure 7B:
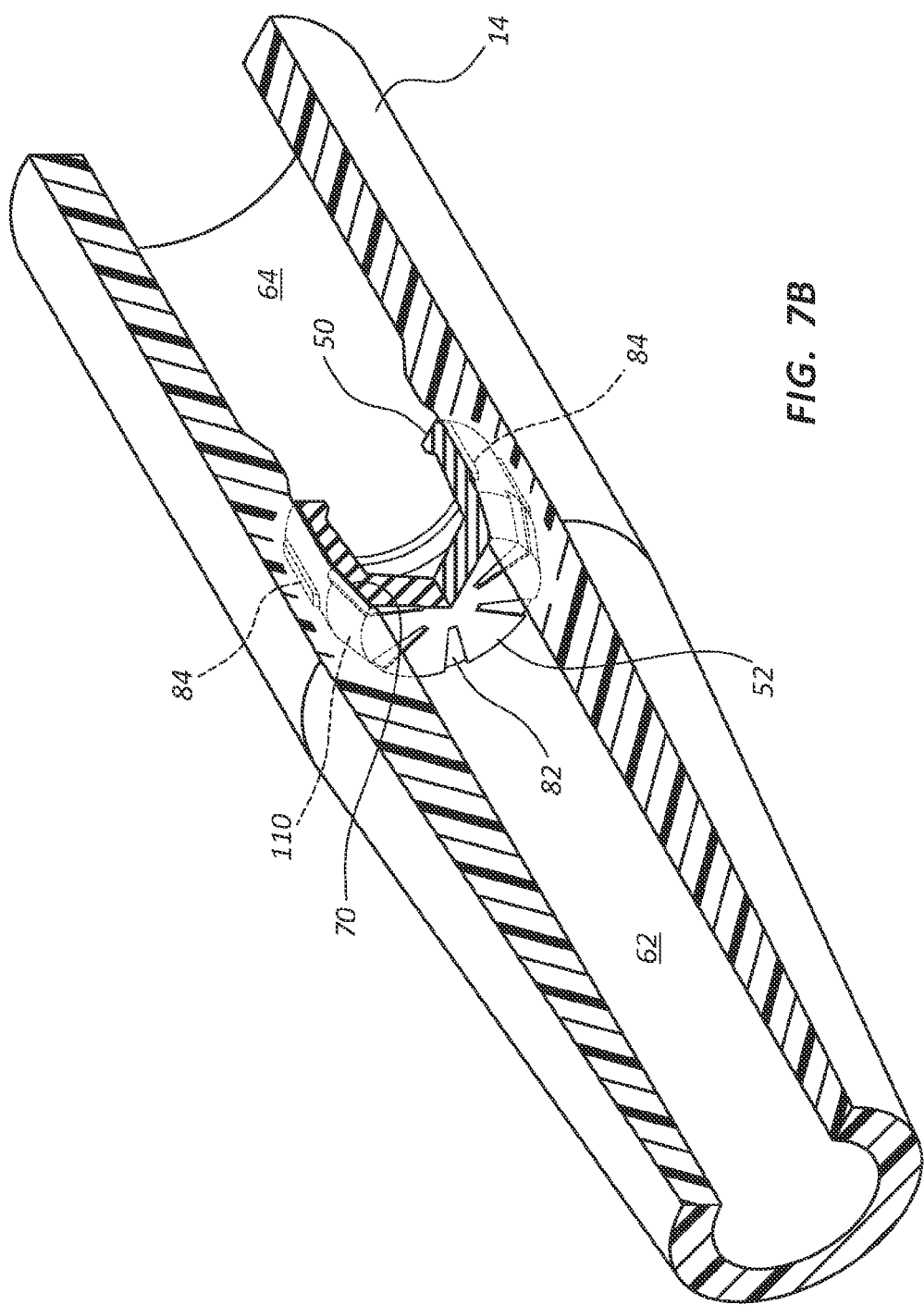

Referring now to FIGS. 7A-7B, in some embodiments the outer circumferential surface of septum 50 comprises a chamfered sealing surface 110. Catheter adapter 14 further comprises a distal ledge 70 that is similarly chamfered so as to form a seal with sealing surface 110. Membrane 52 and chamfered sealing surface 110 further comprise a channel 82 to permit controlled passage of fluids between septum 50 and distal ledge 70. In some embodiments, the non-chamfered portion of the outer circumferential surface of septum 50 further comprises non-sealing centering ribs 84, as shown in FIG. 7B and discussed previously.

Figure 8B:
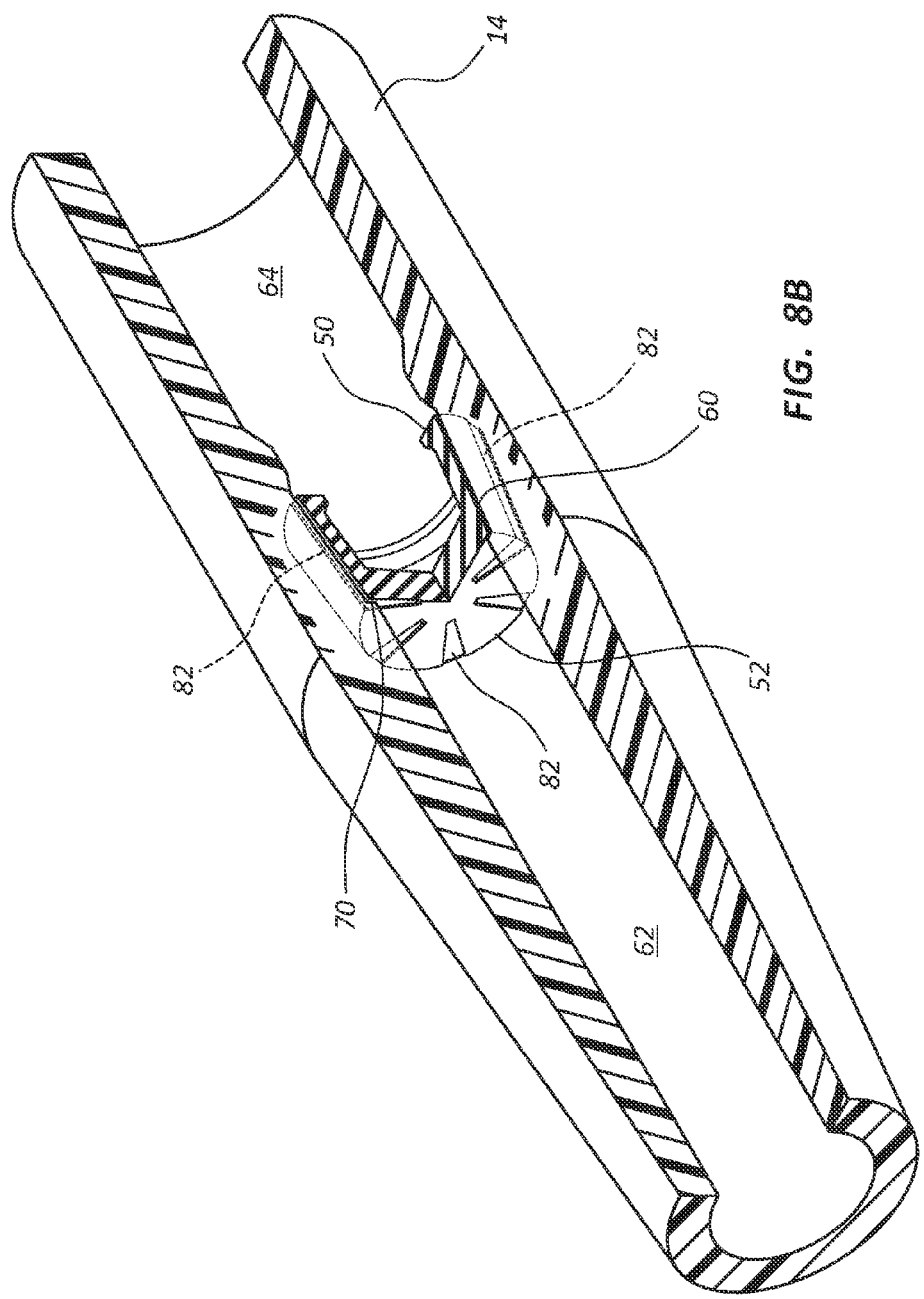
FIG. 8, shown in parts A-B, shows a septum having a tapered sealing surface in accordance with a representative embodiment of the present invention.

In some embodiments, the entire outer circumferential surface, or substantially the outer circumferential surface of septum 50 is chamfered, as shown in FIGS. 8A-8B. Accordingly, in some embodiments septum 50 comprises fluid channels 82 which provide a fluid pathway for fluids to flow between septum 50 and inner surface 60.

Figure 9B:
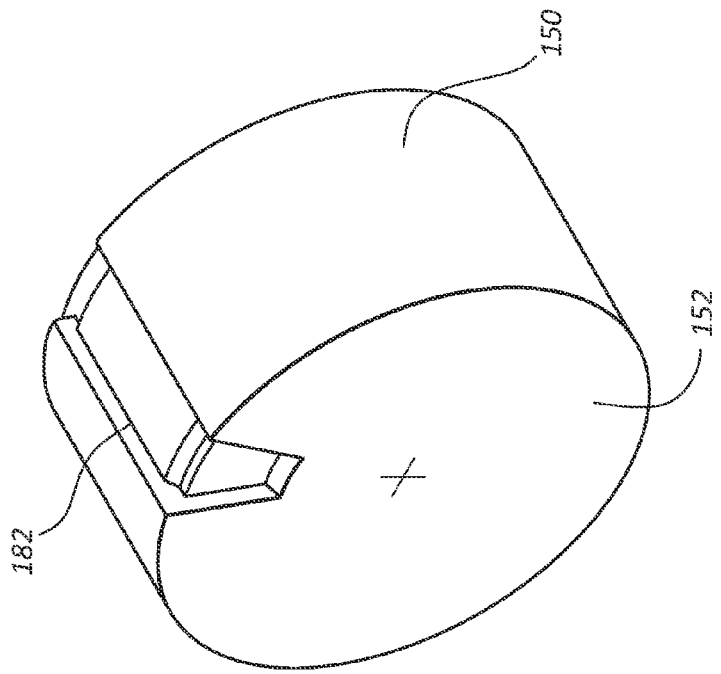
FIG. 9, shown in parts A-F, shows a large vent, slowed flow septum in accordance with a representative embodiment of the present invention.
Figure 9A:
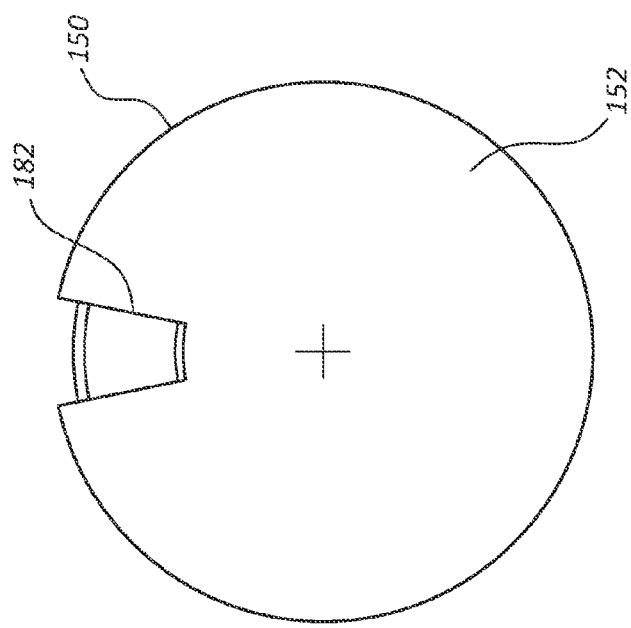
Figure 9C:
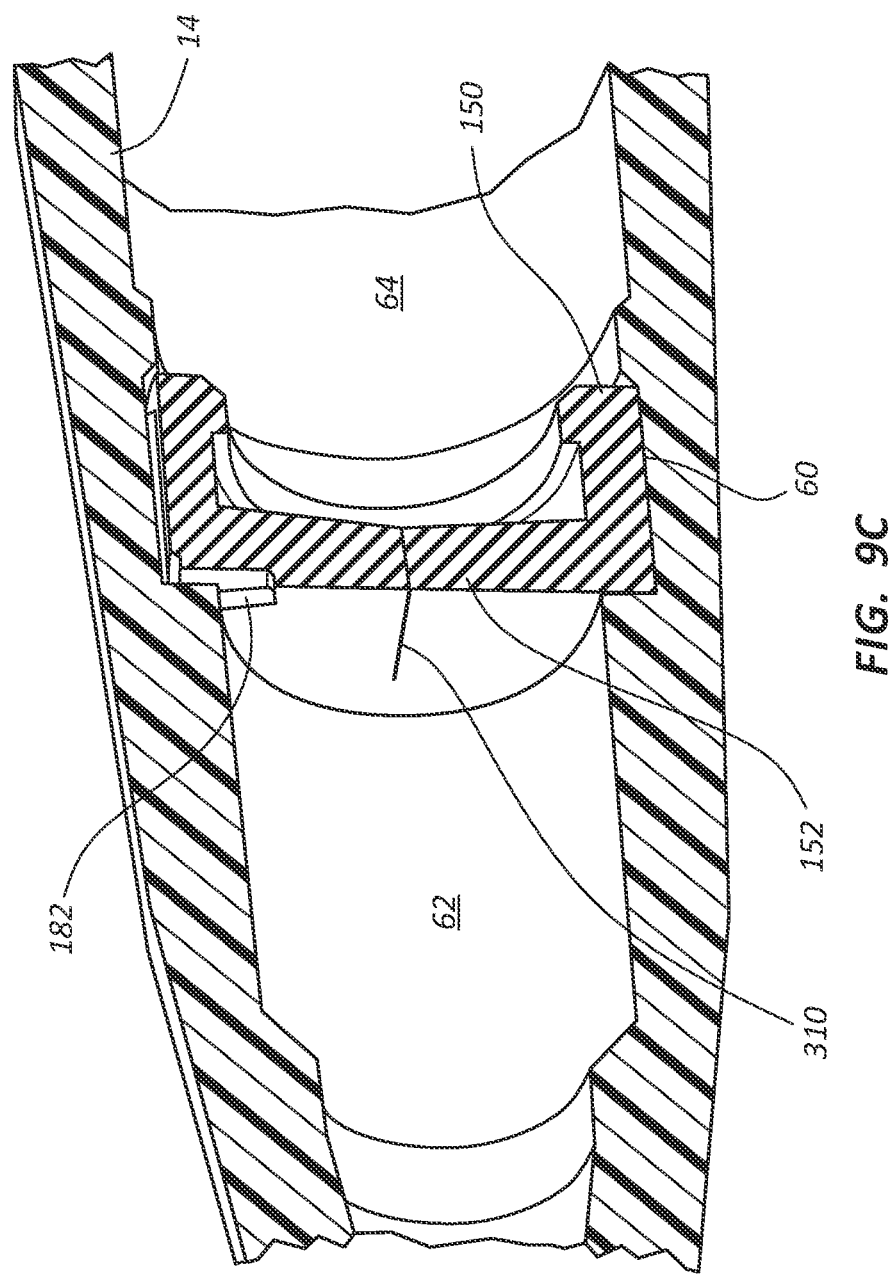
Figure 9D:
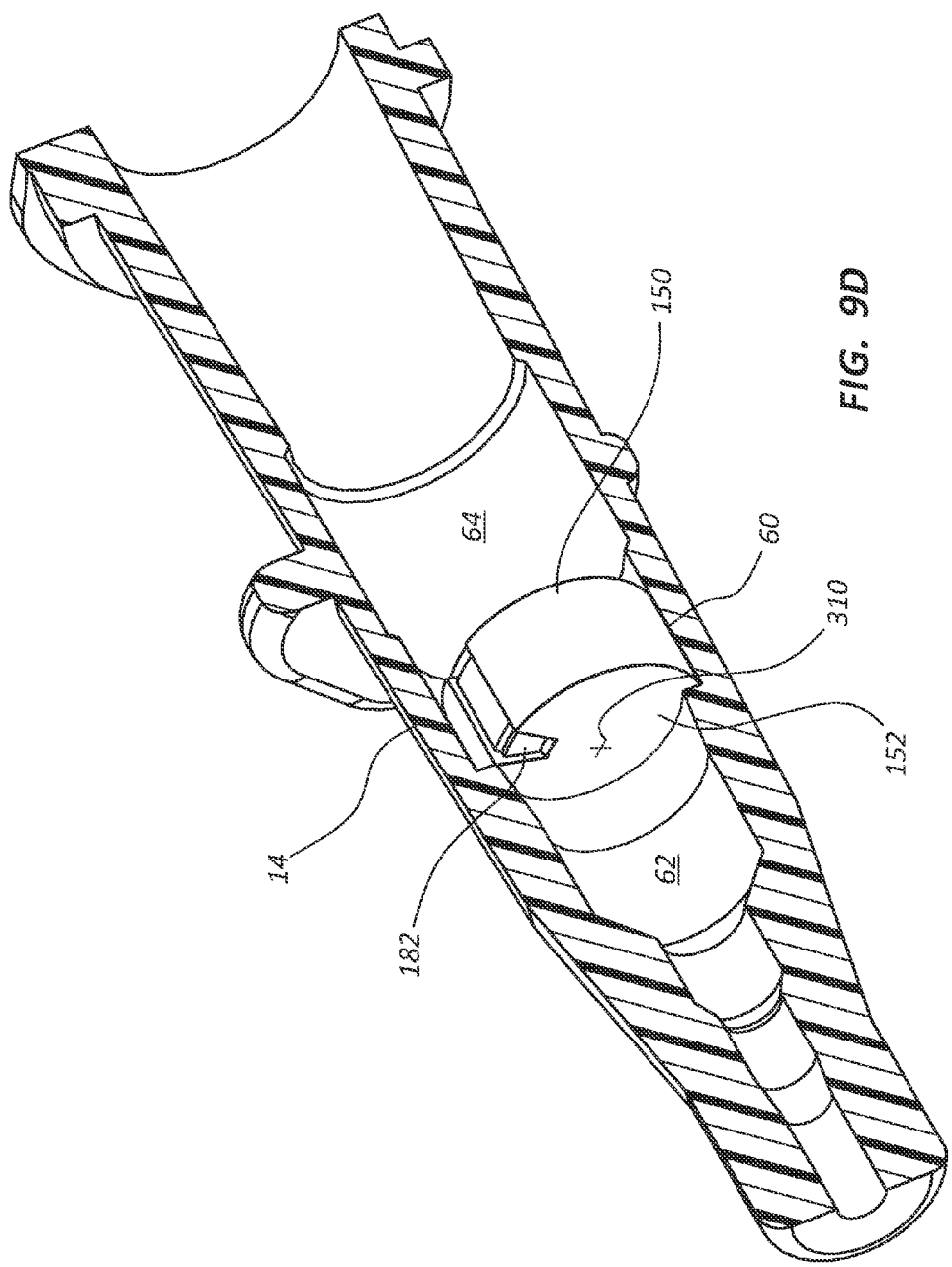

As previously mentioned, in some embodiments a fluid channel is provided to permit controlled flow of fluid between the septum and the inner surface of the catheter adapter. Referring now to FIGS. 9A-9F, a barrel shaped septum 150 is shown having a membrane 152. Septum 150 and membrane 152 further comprise a fluid channel or vent 182 which is provided as a means for allowing fluid to bypass septum 150 and move between the proximal and distal chambers 64 and 62 of the catheter adapter 14. In one sense, septum 150 comprises a single, large sealing surface and a single bypass fluid channel 182, as shown in FIGS. 9A-9D. The size, depth and width of fluid channel 182 determine the rate of fluid flow between proximal and distal chambers 64 and 62. In other embodiments, septum 150 comprises a plurality of fluid channels 182, as shown in FIGS. 9E-9F. One advantage of having a plurality of fluid channels 182 is the elimination of any need for orientation of the septum within inner surface 60. As with the single channel embodiment shown in FIGS. 9A-9F, the fluid channels 182 of the embodiment shown in FIGS. 9E-9F may also be modified in size, depth, width and number to adjust the rate of fluid flow between proximal and distal chambers 64 and 62.

Referring now to FIGS. 10A-10J, some embodiments of the present invention comprise a catheter adapter 14 having an inner surface 60 which is fitted with an insert molded septum 200. Molded septum 200 generally comprises a disk or dish shaped flexible septum having an outer circumferential surface 202. Molded septum 200 further comprises a thin profile thereby allowing for the use of a shortened septum actuator. The thin profile of the molded septum 200 further allows for good flush-ability and may permit a shorter catheter adapter, cannula, barrel and packaging.

In some instances, septum 200 further comprises a skive ring 210 that is molded into outer circumferential surface 202 during the molding process of septum 200, as shown in FIGS. 10A-10H. Skive ring 210 comprises a single ring having an outer diameter sufficient to fixedly wedge septum 200 into a desired position within catheter adapter 14. In some instances, skive ring 210 is molded into septum 200 at an angle that permits insertion of septum 200 into catheter adapter 14 in a distal direction 72, yet prevents movement of septum 200 and skive ring 210 in a proximal direction 75. As such, the angle of skive ring 210 may allow for one-direction insertion of septum 200 into catheter adapter 14. For example, in some embodiments skive ring 210 and septum 200 are inserted into catheter adapter 14 such that septum 200 is seated against sealing surface 290 and the interaction between skive ring 210 and inner surface 60 maintains the seated position of septum 200.

In some embodiments, the outer diameter of skive ring 210 is selected to be slightly greater than the inner diameter of catheter adapter 14 at inner surface 60. As such, skive ring 210 is slightly compressed as skive ring 210 and septum 200 are seated into inner surface 60. In other embodiments, skive ring 210 comprises a material that is harder than the material of catheter adapter 14. Accordingly, as skive ring 210 is forced into catheter adapter 14, skive ring 210 digs into inner surface 60 thereby preventing removal of skive ring 210 and septum 200 in proximal direction 75.

Generally, skive ring 210 is molded into septum 200 such that a portion of skive ring 210 extends radially beyond outer circumferential surface 202 of septum 200. This provides a gap 292 between outer circumferential surface 202 of septum 200 and inner surface 60 of catheter adapter 14, as shown in FIGS. 10A-10D and FIG. 10H. In some embodiments, gap 292 comprises dimensions configured to permit and/or prevent passage of liquid or air.

Generally, skive ring 210 is molded into the outer circumferential surface 202 of septum 200 and retained therein by mechanical interference. In other embodiments, skive ring 210 comprises one or more features 214 configured to increase mechanical engagement between skive ring 210 and septum 200. For example, skive ring 210 may comprise a plurality of holes 214 which increases the surface area of skive ring 210 and which are provided to receive a portion of the septum material during the molding process of septum 200. Thus, holes 214 assist in further interconnecting septum 200 with skive ring 210.

In some instances, skive ring 210 further comprises one or more notches 212 which provide a space between skive ring 210 and inner surface 60 of catheter adapter 14, as shown in FIGS. 10A-10H. Notches 212 may include any dimension as may be required to permit passage of air and/or fluid. In some instances, the dimensions of notches 212 are selected to permit passage of air and prevent passage of fluid. In other embodiments, the dimensions of notches 212 are selected to permit passage of air and/or fluid at a desired flow rate. Further, in some embodiments fluid channel 286 comprises dimensions configured to permit passage of air and fluid, while dimensions of notches 212 are configured to permit passage of air and prevent passage of fluid.

Figure 10B:
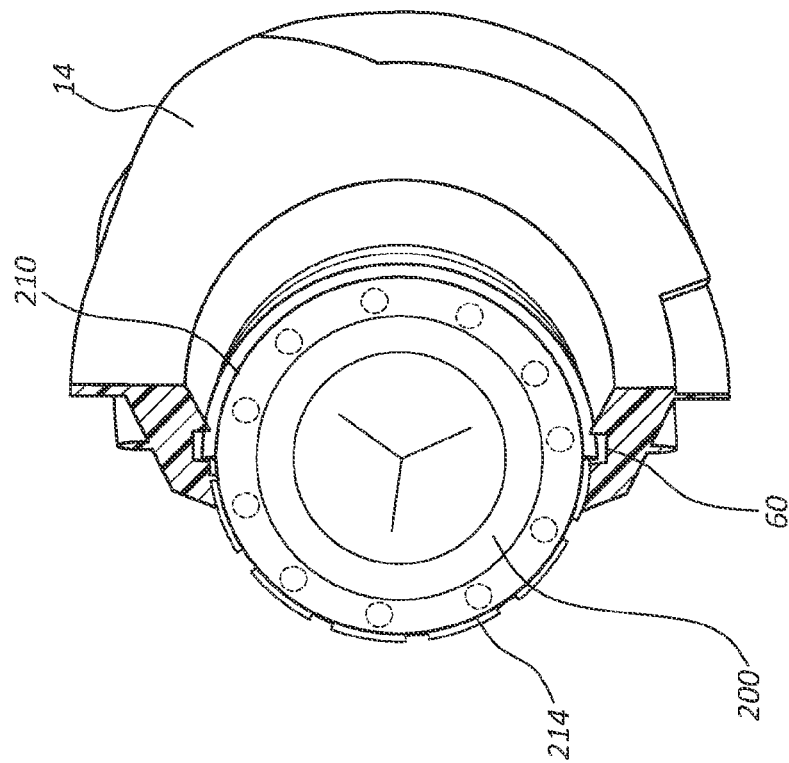
FIG. 10, shown in parts A-J, shows an insert molded septum in accordance with a representative embodiment of the present invention.
Figure 10A:
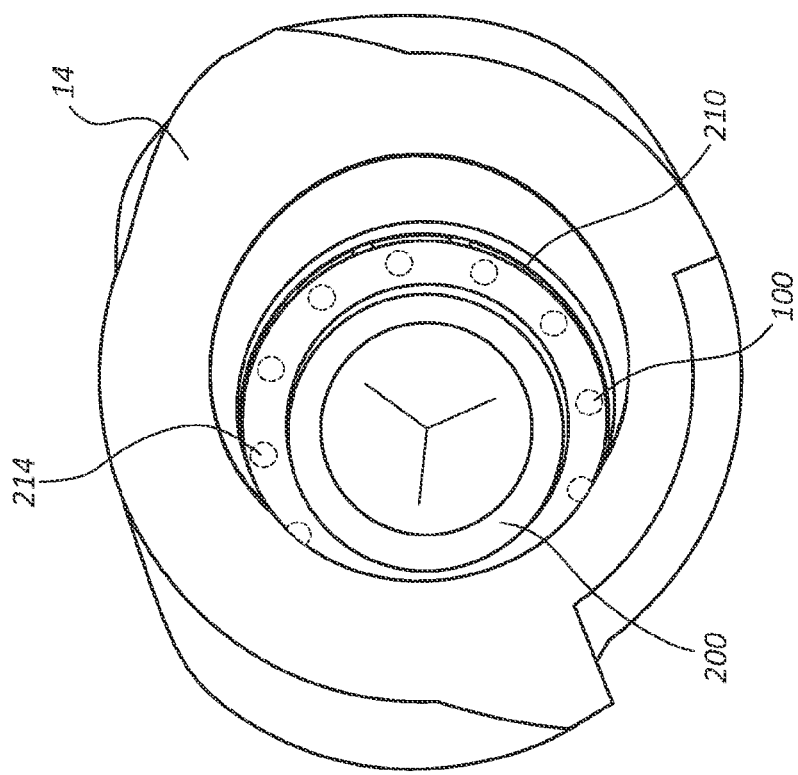
Figure 10C:
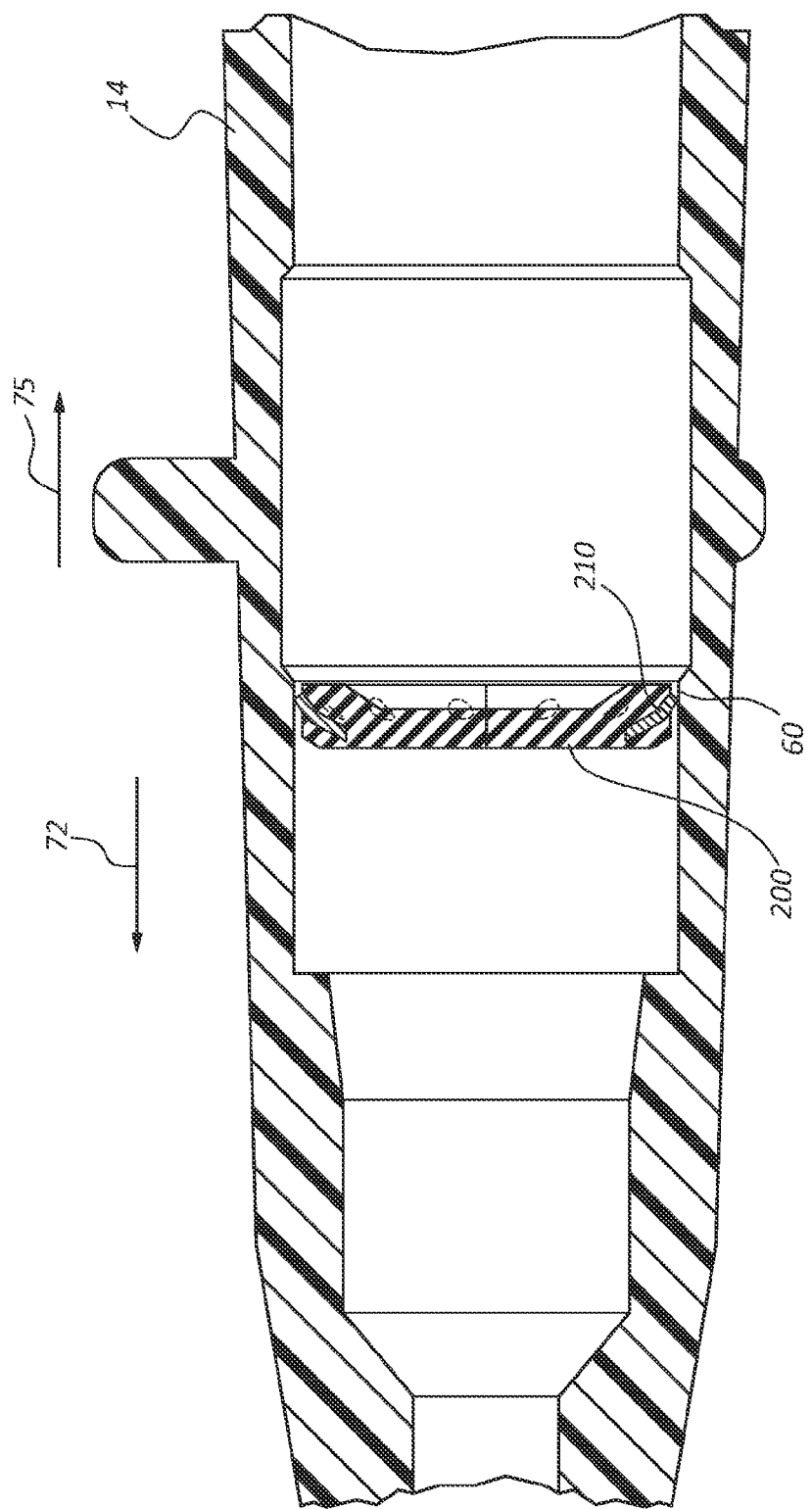
Figure 10E:
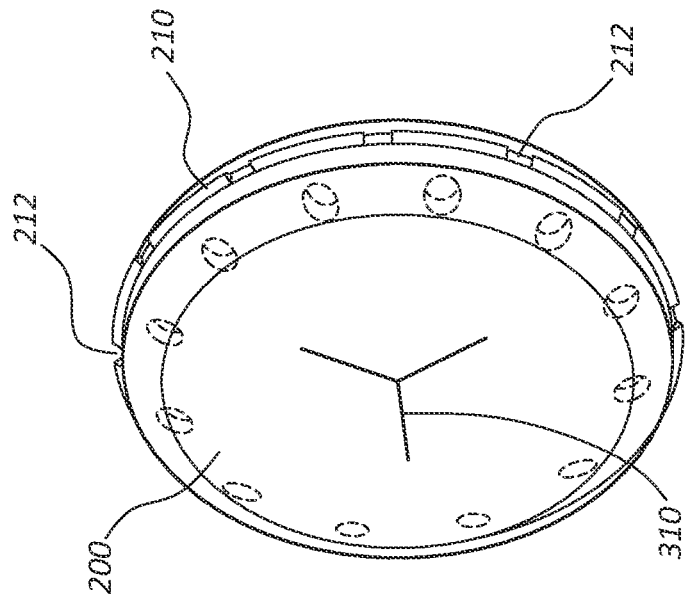
Figure 10D:
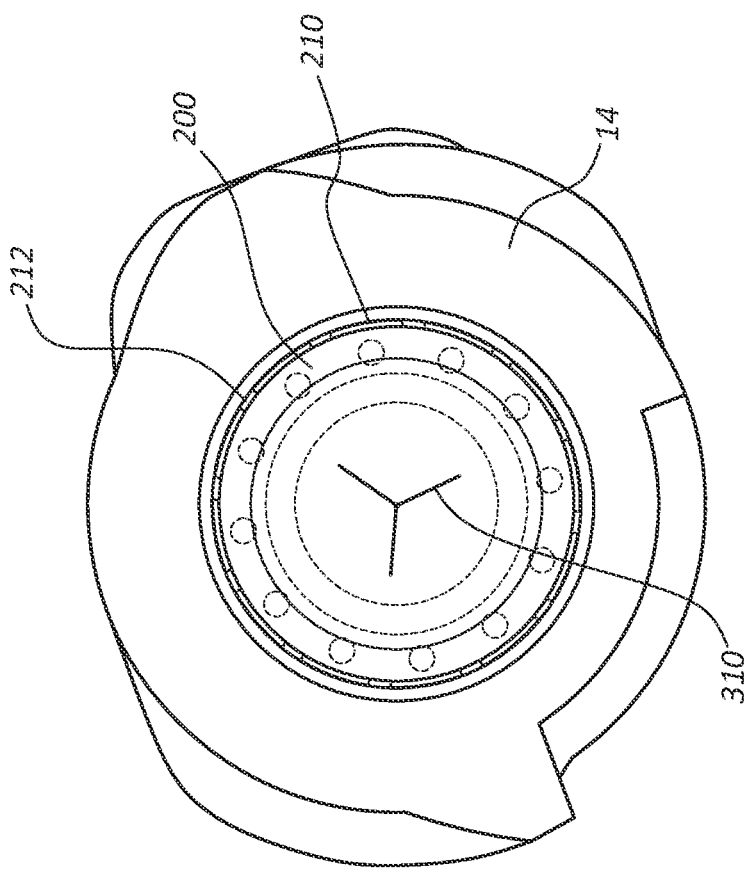
Figure 10I:
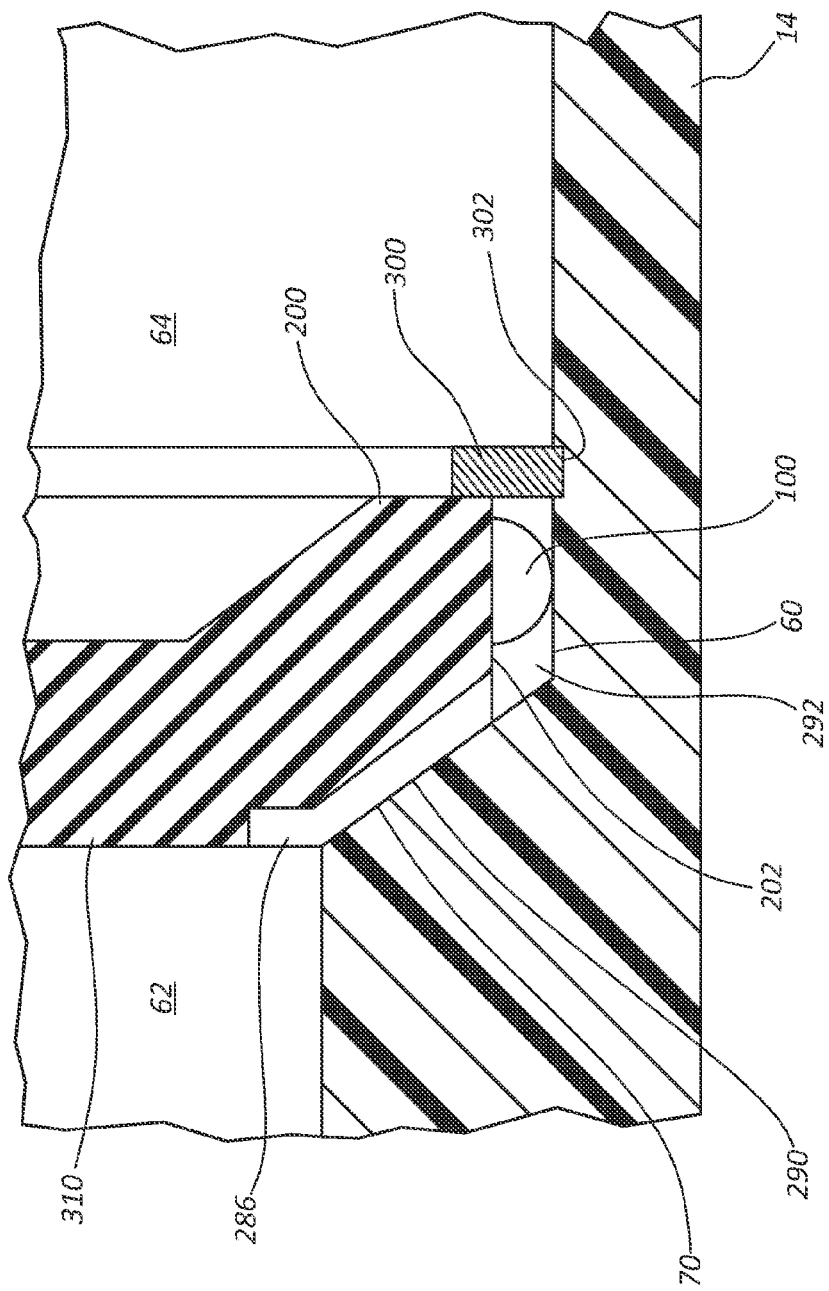

Referring now to FIGS. 10I-10J, some embodiments of septum 200 further comprise one or more centering features 100 such as bumps, ridges, bars or knobs. Molded septum 200 further comprises a fluid channel 286 and sealing surface 290. Sealing surface 290 forms a seal with distal ledge 70, while fluid channel 286 permits passage of fluid between molded septum 200 and distal edge 70. Centering feature 100 further provides a gap 292 thereby providing passage of fluid between the outer circumferential surface of septum 200 and inner surface 60. In some embodiments, sealing surface 290 further includes centering features 100 in place of, or in addition to fluid channels 286.

In some embodiments, molded septum 200 is retained in place via a retention ring 300. Retention ring 300 is positioned and retained in a groove 302 formed on an inner surface 60. In some embodiments, retention ring 300 further comprises a plurality of notches 312 to permit fluid passage through retention ring 300. Molded septum 200 may further include a slit 310 to permit passage of an introducer needle or other probe device.

Figure 11:
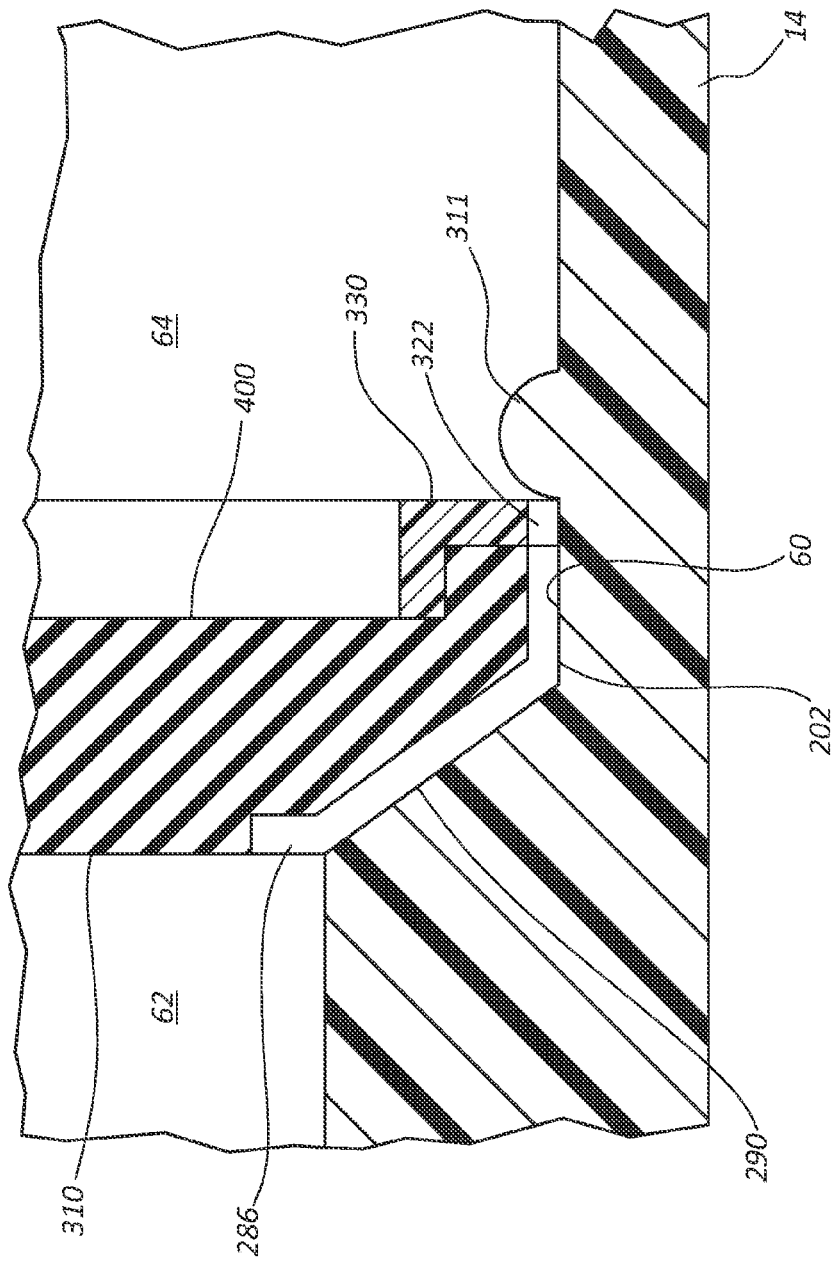
FIG. 11 is a cross-section of a catheter adapter comprising a compact molded septum secured by a snap ring in accordance with a representative embodiment of the present invention.

Referring now to FIG. 11, in some embodiments catheter adapter 14 further comprises a positive feature 311, such as an annular ring protrusion that is configured to receive snap ring 330 to secure molded septum 400 in place. In some instances, snap ring 330 comprises a plurality of channels or vents 322 to permit passage of air or fluid from fluid channel 286. In some embodiments, vents 322 are sized to permit passage of air while preventing passage of fluid. For example, vents 322 may comprise a cross-section area that prevents passage of a fluid due to surface tension.

Snap ring 330 may comprise any biocompatible material having physical properties sufficient to retain septum 400 in a desired position within catheter adapter 14. For example, snap ring 330 may comprise a plastic or polymer material, a metallic material and/or a composite material. Snap ring 330 may further comprise a coating to prevent bacterial colonization.

Figure 12:
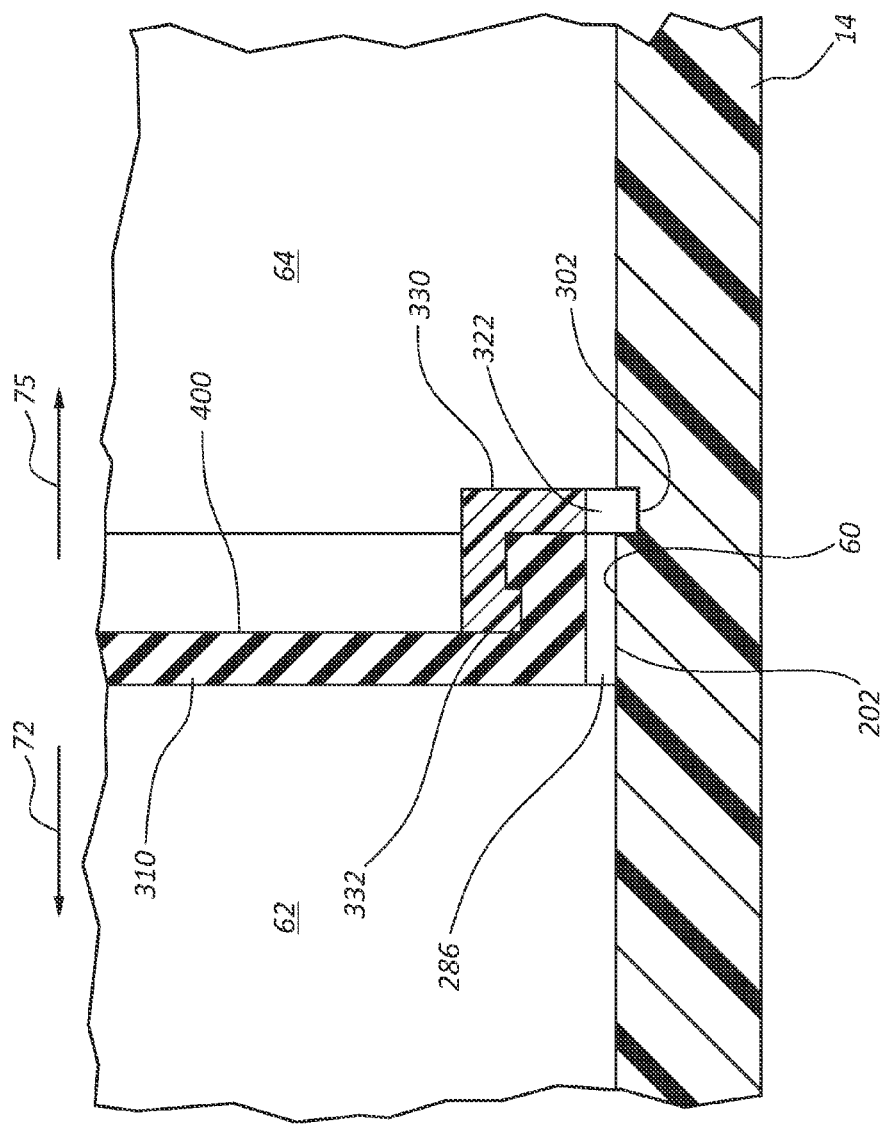
FIG. 12 is a cross-section of a catheter adapter comprising a compact molded septum secured by a snap ring having a clip in accordance with a representative embodiment of the present invention.

Further still, in some embodiments, snap ring 330 may include a clip 332 that is configured to interconnect snap ring 330 with molded septum 400, as shown in FIG. 12. Snap ring 330 is further seated into a groove 302 formed on inner surface 60, thereby preventing movement of septum 400 and snap ring 330 in distal and/or proximal directions 72 and 75. The desired location of septum 400 may be achieved through placement of groove 302. In some embodiments, a fluid channel 286 is provided between molded septum 400 and the inner wall surface of catheter adapter 14. Further, in some embodiments snap ring 330 comprises one or more notches 322 to permit controlled passage of air and/or fluid through snap ring 330.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An intravenous catheter assembly comprising: a catheter adapter having an inner surface forming a lumen, the inner surface including a distal ledge; and a septum having a proximal end, a distal end forming a distal membrane, and an outer surface, an outer portion of a surface of the distal membrane forming a seal with the distal ledge of the catheter adapter thereby creating a distal chamber and a proximal chamber within the lumen, the septum comprising one or more non-sealing centering ribs that extend along a length of the outer surface to space the outer surface of the septum from the inner surface of the catheter adapter; the septum further comprising one or more fluid pathways, each fluid pathway comprising a recess formed into the surface of the distal membrane from an inner portion of the surface of the distal membrane along the outer portion of the surface of the distal membrane and to the outer surface of the septum thereby allowing fluid or air within the distal chamber to bypass the seal formed between the outer portion of the surface of the distal membrane and the distal ledge and flow around the outer surface of the septum and into the proximal chamber.

2. The assembly of claim 1, further comprising a snap ring having a first surface that is in contact with an inner surface of the catheter adapter, and further comprising a second surface that is in contact with the septum.

3. The assembly of claim 1, wherein the outer portion of the surface of the distal membrane of the septum is chamfered.

4. The assembly of claim 1, wherein the distal ledge of the catheter adapter is chamfered.

5. The assembly of claim 1, wherein the one or more fluid pathways comprise a plurality of fluid pathways.

6. The assembly of claim 2, wherein the recess of each fluid pathway passes through the snap ring.

7. The assembly of claim 1, wherein the distal ledge comprises a vertical front face distal ledge and the distal membrane comprises a planar membrane.

8. The assembly of claim 1, wherein the distal ledge comprises a lip that extends in a proximal direction and the outer portion of the surface of the distal membrane extends in a distal direction.

9. An intravenous catheter assembly comprising: a catheter adapter having an inner surface forming a lumen, the inner surface holding a distal ledge; and a septum having a proximal end, a distal end forming a distal membrane, and an outer surface, an outer portion of a surface of the distal membrane forming a seal with the distal ledge of the catheter adapter and the outer surface of the septum forming a seal with the inner surface of the catheter adapter thereby creating a distal chamber and a proximal chamber within the lumen, the septum comprising one or more fluid pathways, each fluid pathway comprising a recess formed into the surface of the distal membrane and the outer surface of the septum, the recess extending radially along the surface of the distal membrane from an inner portion of the surface of the distal membrane along the outer portion of the surface of the distal membrane and the outer surface of the septum to the proximal end of the septum thereby allowing fluid or air within the distal chamber to bypass the seal formed between the outer portion of the surface of the distal membrane and the distal ledge and the seal formed between the outer surface of the septum and the inner surface of the catheter adapter and flow into the proximal chamber.

10. The assembly of claim 9, wherein the outer surface of the septum and the inner surface of the catheter adapter are chamfered.

11. The assembly of claim 9, wherein the one or more fluid pathways comprise a plurality of fluid pathways.

12. An intravenous catheter assembly comprising: a catheter adapter having an inner surface forming a lumen, the inner surface including a distal ledge; and a septum having a proximal end, a distal end forming a distal membrane, and an outer surface, an outer portion of a surface of the distal membrane forming a seal with the distal ledge of the catheter adapter thereby creating a distal chamber and a proximal chamber within the lumen, the septum further comprising one or more fluid pathways, each fluid pathway comprising a recess formed into the surface of the distal membrane that extends radially along the surface of the distal membrane from an inner portion of the surface of the distal membrane along the outer portion of the surface of the distal membrane and to the outer surface of the septum thereby allowing fluid or air within the distal chamber to bypass the seal formed between the outer portion of the surface of the distal membrane and the distal ledge and flow around the outer surface of the septum and into the proximal chamber.

13. The assembly of claim 11, wherein the septum further comprising one or more non-sealing centering ribs that extend along a length of the outer surface to space the outer surface of the septum from the inner surface of the catheter adapter.

14. The assembly of claim 12, wherein the septum further comprises one or more bumps that are positioned on the outer surface of the septum to space the outer surface from the inner surface of the catheter adapter.

15. The assembly of claim 12, wherein the distal ledge and the outer portion of the surface of the distal membrane are chamfered.

16. The assembly of claim 12, wherein the distal ledge comprises a lip that extends in a proximal direction and the outer portion of the surface of the distal membrane extends in a distal direction.

\* \* \* \* \*